(12) United States Patent
MacDonald et al.

(10) Patent No.: US 9,174,953 B2
(45) Date of Patent: Nov. 3, 2015

(54) BICYCLIC THIAZOLES AS ALLOSTERIC MODULATORS OF MGLUR5 RECEPTORS

(75) Inventors: Gregor James MacDonald, Zoersel (BE); Gary John Tresadern, Toledo (ES); Andrés Avelino Trabanco-Suárez, Olias del Rey (ES); Joaquin Pastor-Fernández, Toledo (ES)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 13/516,968

(22) PCT Filed: Dec. 16, 2010

(86) PCT No.: PCT/EP2010/069972
§ 371 (c)(1),
(2), (4) Date: Jun. 18, 2012

(87) PCT Pub. No.: WO2011/073347
PCT Pub. Date: Jun. 23, 2011

(65) Prior Publication Data
US 2012/0252800 A1 Oct. 4, 2012

(30) Foreign Application Priority Data

Dec. 18, 2009 (EP) .................... 09179850

(51) Int. Cl.
| C07D 513/04 | (2006.01) |
| A61K 31/4365 | (2006.01) |
| C07D 277/60 | (2006.01) |
| C07D 417/04 | (2006.01) |
| C07D 417/06 | (2006.01) |
| C07D 417/12 | (2006.01) |

(52) U.S. Cl.
CPC .......... *C07D 277/60* (2013.01); *A61K 31/4365* (2013.01); *C07D 417/04* (2013.01); *C07D 417/06* (2013.01); *C07D 417/12* (2013.01); *C07D 513/04* (2013.01)

(58) Field of Classification Search
CPC .......................... C07D 513/04; A61K 31/4365
USPC .......................... 546/114; 514/301
See application file for complete search history.

(56) References Cited

U.S. PATENT DOCUMENTS

| 5,753,664 | A | 5/1998 | Aono et al. |
| 7,893,069 | B2 | 2/2011 | Kuehnert et al. |
| 8,242,116 | B2 * | 8/2012 | Alexander et al. ......... 514/234.2 |
| 2009/0163545 | A1 | 6/2009 | Goldfarb |
| 2010/0081690 | A1 | 4/2010 | LePoul et al. |
| 2013/0029904 | A1 | 1/2013 | Kukolj |

FOREIGN PATENT DOCUMENTS

| JP | 2000-108513 | 4/2000 | |
| JP | 03066110 | 7/2000 | |
| JP | 2002-105085 | 4/2002 | |
| JP | 2006-513996 | 4/2006 | |
| JP | 2009-514923 | 4/2009 | |
| WO | WO 2004/038374 | 5/2004 | |
| WO | WO 2005/082856 | 9/2005 | |
| WO | WO 2006/066174 | 6/2006 | |
| WO | WO 2006/074884 | 7/2006 | |
| WO | WO 2007/007040 | 1/2007 | |
| WO | WO 2007/023242 | 3/2007 | |
| WO | WO 2007/023290 | 3/2007 | |
| WO | WO 2007/056366 | 5/2007 | |
| WO | WO 2007/104485 | 9/2007 | |
| WO | WO 2008/012010 | 1/2008 | |
| WO | WO 2008001076 A1 * | 1/2008 | .......... C07D 513/04 |
| WO | WO 2008/060597 | 5/2008 | |
| WO | WO 2008/066174 | 6/2008 | |
| WO | WO 2008/076562 | 6/2008 | |
| WO | WO 2008/151184 | 12/2008 | |
| WO | WO 2010/114971 | 10/2010 | |
| WO | 2011/072370 | 6/2011 | |
| WO | WO 2011/073339 | 6/2011 | |

OTHER PUBLICATIONS

Database Beilstein, (Jan. 2010) XP002580527, No. BRN977498, Lehmann G.et al.
Stepanov et al., 2002, Database Caplus XP 002580528, Accession nr. 2002:250236, RN 441771-46-6, RN 312526-80-0.
International Search Report for PCT/EP2010/069972 dated Apr. 5, 2011.
Billingsley, et al., J. Org. Chem. 2008, 73(14), 5589-5591.
Chinchilla et al., Chem. Rev. 2007, 107(3), 874-922.
Chrovian et al., Org. Lett. 2008, 10(5), 811-814.
Collison et al., Synthesis, 2006, 14, 2319-2322.
Kew and Kemp Psychopharmacol., 2005, 179:4-29.
Mutel, Expert Opin. Ther. Patents, 2002, 12:1-8.
Orita et al., Chem. Rev. 2006, 106(12), 5387-5412.
Roppe et al.; Bioorganic & Medicinal Chem. 14, 3993-3996 (2004).
Schoepp D. D. et al. Neuropharmacology, 1999, 38(10), 1431-1476.
Takagi et al., J. Am. Chem. Soc. 2002, 124(27), 8001-8006.
Valgeirsson et al.; Bioorganic & Medicinal Chem. 11, 4341-4349 (2003).
Cozzoli et al., J Neurosci. Jul. 8, 2009; 29(27): 8655-8668.
Liu et al., Journal of Neurochemistry, 2005, 95, 1363-1372.

* cited by examiner

*Primary Examiner* — David K O Dell
(74) *Attorney, Agent, or Firm* — Hal B. Woodrow

(57) ABSTRACT

The present invention relates to novel bicyclic thiazoles which are positive allosteric modulators of the metabotropic glutamate receptor subtype 5 ("mGluR5") and which are useful for the treatment or prevention of disorders associated with glutamate dysfunction and diseases in which the mGluR5 subtype of receptors is involved. The invention is also directed to pharmaceutical compositions comprising such compounds, to processes for preparing such compounds and compositions, and to the use of such compounds and compositions for the prevention and treatment of disorders in which mGluR5 is involved.

7 Claims, No Drawings

BICYCLIC THIAZOLES AS ALLOSTERIC MODULATORS OF MGLUR5 RECEPTORS

CROSS REFERENCE TO RELATED APPLICATIONS

This application is the national stage of PCT Application No. PCT/EP2010/069972, filed Dec. 16, 2010, which claims priority from European Patent Application No. 09179850.4, filed Dec. 18, 2009, the entire disclosures of which are hereby incorporated in their entirety.

FIELD OF THE INVENTION

The present invention relates to novel bicyclic thiazoles which are positive allosteric modulators of the metabotropic glutamate receptor subtype 5 ("mGluR5") and which are useful for the treatment or prevention of disorders associated with glutamate dysfunction and diseases in which the mGluR5 subtype of receptors are involved. The invention is also directed to pharmaceutical compositions comprising such compounds, to processes for preparing such compounds and compositions, and to the use of such compounds and compositions for the prevention and treatment of disorders in which mGluR5 is involved.

BACKGROUND OF THE INVENTION

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptors channels (iGluRs), and the NMDA, AMPA and kainate receptors which are responsible for fast excitatory transmission (Kew and Kemp Psychopharmacol., (2005), 179:4-29).

In addition, glutamate activates metabotropic glutamate receptors (mGluRs) which have a more modulatory role that contributes to the fine-tuning of synaptic efficacy.

Glutamate activates the mGluRs through binding to the large extracellular amino-terminal domain of the receptor, herein called the orthosteric binding site. This binding induces a conformational change in the receptor which results in the activation of the G-protein and intracellular signaling pathways.

mGluR5 and NMDA receptors are co-expressed in hippocampus, cortex and striatum.

mGluR5 potentiates NMDA receptor function via a PKC- and Src-dependent mechanism. Blockade of mGluR5 or NMDA receptors impairs cognitive function whereas activation of mGluR5 or NMDA receptors normalizes amphetamine disrupted pre-pulse inhibition (PPI). Stimulation of mGluR5 receptors is postulated to normalize the NMDA receptor hypofunction in schizophrenia. An mGluR5 positive allosteric modulator (PAM) may have beneficial effects on cognition, positive and negative symptoms of schizophrenia, and cognitive deficits in various forms of dementia and mild cognitive impairment.

To date, most of the available pharmacological tools targeting mGluRs are orthosteric ligands which cross react with several members of the family as they are structural analogues of glutamate and have limited bioavailability (Schoepp D. D. et al. Neuropharmacology (1999), 38(10), 1431-1476). A new avenue for developing selective compounds acting at mGluRs is to identify molecules that act through allosteric mechanisms, modulating the receptor by binding to a site different from the highly conserved glutamate binding site. Positive allosteric modulators of mGluRs have emerged recently as novel pharmacological entities offering this attractive alternative. This type of molecule has been discovered for several mGluR sub-types (reviewed in Mutel (2002) Expert Opin. Ther. Patents 12:1-8).

WO-2005/082856, WO-2007/023242 and WO-2007/023290 (Merz) disclose tetrahydroquinolinones as modulators of Group I mGluRs. WO 2008/151184 (Vanderbilt University) discloses benzamides as mGluR5 positive allosteric modulators. Fused thiazole compounds are further known from amongst others WO-2008/060597 (Vertex), WO-2008/076562 (Lilly), WO-2008/001076 (UCB), WO-2008/066174 (Lilly) and WO-2006/066174 (Eli Lilly). US 2010/0081690 (Addex Pharma, S.A.) published on Apr. 1, 2010 discloses oxazole derivatives as positive allosteric modulators of mGluR5. WO 2008/012010 (UCB Pharma, S.A.) published on Jan. 31, 2008 discloses fused oxazoles and thiazoles as Histamine H3-receptor ligands with groups at the 2-position of the thiazole ring that are different to the ones disclosed herein. WO 2010/114971 (Sepracor Inc.), published on Oct. 7, 2010 discloses bicyclic compounds and provides data for their activity as mGluR5NAMs; none of the exemplified compounds contain a carbonyl group in the bicyclic core.

It is the object of the present invention to provide novel compounds with an improved balance of properties over the prior compounds, in particular, advantageous properties such as a good absorption, distribution, metabolism and excretion (AdMe) profile, good stability and permeability as measured for example, in the parallel artificial membrane permeability assay (PAMPA).

DESCRIPTION OF THE INVENTION

The present invention relates to compounds having metabotropic glutamate receptor 5 modulator activity, said compounds having the Formula (I)

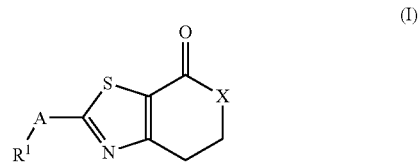

and the stereoisomeric forms thereof,
wherein
X is selected from $CH_2$ and $NR^2$;
A is selected from the group consisting of 1,2-ethanediyl; 1,2-ethenediyl; and 1,2-ethynediyl;
$R^1$ is selected from the group consisting of phenyl; phenyl substituted with 1 or 2 halo substituents; pyridinyl; and pyridinyl substituted with 1 or two halo substituents;
or $R^1$-A together is 3,4-dihydro-2H-1,4-benzoxazin-7-yl optionally substituted with methyl;
$R^2$ is selected from the group consisting of hydrogen; methyl; methoxyethyl; aryl; benzyl; and benzyl wherein the phenyl part is substituted with 1 or 2 halo substituents;

wherein aryl is phenyl, optionally substituted with 1 or 2 substituents selected from the group consisting of methyl, methoxy, cyano, fluoro, chloro, trifluoromethyl and trifluoromethyloxy;

and the pharmaceutically acceptable salts and the solvates thereof.

The present invention also relates to a pharmaceutical composition comprising a therapeutically effective amount of a compound of Formula (I) and a pharmaceutically acceptable carrier or excipient.

Additionally, the invention relates to a compound of Formula (I) for use as a medicament and to a compound of Formula (I) for use as a medicament for the treatment or prevention of neurological and psychiatric disorders in which mGluR5 is involved.

The invention also relates to the use of a compound according to Formula (I) or a pharmaceutical composition according to the invention for the manufacture of a medicament for treating or preventing neurological and psychiatric disorders in which mGluR5 is involved.

Additionally, the invention relates to the use of a compound of Formula (I) in combination with an additional pharmaceutical agent for the manufacture of a medicament for treating or preventing neurological and psychiatric disorders in which mGluR5 is involved.

Furthermore, the invention relates to a process for preparing a pharmaceutical composition according to the invention, characterized in that a pharmaceutically acceptable carrier is intimately mixed with a therapeutically effective amount of a compound of Formula (I).

The invention also relates to a product comprising a compound of Formula (I) and an additional pharmaceutical agent, as a combined preparation for simultaneous, separate or sequential use in the prevention, treatment or prophylaxis of neurological and psychiatric disorders and diseases.

The chemical names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006). In case of tautomeric forms, the name of the depicted tautomeric form of the structure was generated. However, it should be clear that the other non-depicted tautomeric form is also included within the scope of the present invention.

DETAILED DESCRIPTION OF THE INVENTION

Definitions

The term "halogen" or "halo" as used herein alone or as part of another group refers to fluorine, chlorine, bromine or iodine, with fluorine or chlorine being preferred, and fluoro being particularly preferred.

The term "alkyl" as employed herein alone or as part of another group, unless otherwise stated, refers to a saturated straight or branched hydrocarbon chain radical which includes but is not limited to methyl, ethyl, 1-propyl, 1-butyl, 1-pentyl, 1-methylethyl, 1,1-dimethylethyl, 2-methylpropyl, 3-methylbutyl, 1,2-dimethylpropyl, 1-hexyl, 1,2,2-trimethylpropyl, 1-ethyl-2,2-dimethylpropyl, 1,1,2,2-tetramethylpropyl, 1-heptyl and 1-octyl.

The term "$C_{1-3}$alkanediyl" as employed herein alone or as part of another group unless otherwise stated refers to a bivalent straight or branched chain saturated hydrocarbon radical having from 1 to 3 carbon atoms such as, for example, methylene; 1,2-ethanediyl; 1,3-propanediyl; and the branched isomers thereof.

In another embodiment, the invention relates to compounds of formula (I) wherein
X is selected from $CH_2$ and $NR^2$;
A is selected from the group consisting of 1,2-ethanediyl; 1,2-ethenediyl; and 1,2-ethynediyl;
$R^1$ is selected from the group consisting of phenyl; phenyl substituted with 1 or 2 halo substituents; pyridinyl; and pyridinyl substituted with 1 or two halo substituents;
or $R^1$-A together is 3,4-dihydro-2H-1,4-benzoxazin-7-yl optionally substituted with methyl;
$R^2$ is selected from the group consisting of hydrogen; methyl; methoxyethyl; benzyl; and benzyl wherein the phenyl part is substituted with 1 or 2 halo substituents;
and the pharmaceutically acceptable salts and the solvates thereof.

In an additional embodiment, the invention relates to compounds of formula (I) wherein
X is selected from $CH_2$ and $NR^2$;
A is selected from the group consisting of 1,2-ethenediyl; and 1,2-ethynediyl;
$R^1$ is selected from the group consisting of phenyl; phenyl substituted with 1 or 2 halo substituents; pyridinyl; and pyridinyl substituted with 1 or two halo substituents;
or $R^1$-A together is 3,4-dihydro-2H-1,4-benzoxazin-7-yl optionally substituted with methyl;
$R^2$ is selected from the group consisting of hydrogen; methyl; methoxyethyl; benzyl; and benzyl wherein the phenyl part is substituted with 1 or 2 halo substituents;
and the pharmaceutically acceptable salts and the solvates thereof.

In another embodiment, the invention relates to compounds of formula (I) wherein
X is selected from $CH_2$ and $NR^2$;
A is selected from the group consisting of 1,2-ethenediyl; and 1,2-ethynediyl;
$R^1$ is selected from the group consisting of phenyl; pyridinyl; and pyridinyl substituted with 1 or two fluoro substituents;
or $R^1$-A together is 3,4-dihydro-2H-1,4-benzoxazin-7-yl optionally substituted with methyl;
$R^2$ is selected from the group consisting of hydrogen; methyl; methoxyethyl; benzyl; and benzyl wherein the phenyl part is substituted with 1 or 2 fluoro substituents;
and the pharmaceutically acceptable salts and the solvates thereof.

In another preferred embodiment, the invention relates to compounds of formula (I) wherein
X is selected from $CH_2$ and $NR^2$;
A is selected from the group consisting of 1,2-ethenediyl; and 1,2-ethynediyl;
$R^1$ is selected from the group consisting of phenyl; pyridinyl; and pyridinyl substituted with 1 or two fluoro substituents;
or $R^1$-A together is 3,4-dihydro-2H-1,4-benzoxazin-7-yl optionally substituted with methyl;
$R^2$ is selected from the group consisting of hydrogen; methyl; methoxyethyl; and benzyl;
and the pharmaceutically acceptable salts and the solvates thereof.

In another embodiment, the invention relates to compounds of formula (I) wherein
X is selected from $CH_2$ or $NR^2$;
A is selected from the group consisting of 1,2-ethenediyl; and 1,2-ethynediyl;
$R^1$ is selected from the group consisting of phenyl; pyridin-3-yl; and 5-fluoro-pyridin-3-yl;

$R^2$ is selected from the group consisting of hydrogen; methyl; 2-methoxyethyl; and benzyl;

and the pharmaceutically acceptable salts and the solvates thereof.

In one embodiment X is $NR^2$.

In one embodiment X is $CH_2$.

In one embodiment, A is selected from 1,2-ethenediyl and 1,2-ethynediyl.

In one embodiment, A is 1,2-ethynediyl.

In another embodiment, $R^1$-A together is 3,4-dihydro-2H-1,4-benzoxazin-7-yl substituted with methyl when X is $CH_2$.

In another embodiment, $R^1$ is selected from the group consisting of phenyl and pyridinyl optionally substituted with a fluoro substituent when X is $CH_2$.

In another embodiment, $R^1$ is pyridinyl optionally substituted with a fluoro substituent when X is $CH_2$.

In another embodiment, $R^1$ is 5-fluoro-3-pyridinyl when X is $CH_2$.

In another embodiment, $R^1$ is phenyl.

In another embodiment, $R^2$ is selected from the group consisting of hydrogen, methyl, 2-methoxyethyl and benzyl.

In yet another preferred embodiment, $R^2$ is selected from the group consisting of methyl; methoxyethyl; and benzyl.

In another embodiment, $R^2$ is 2-methoxyethyl.

In another embodiment, $R^2$ is H.

In another embodiment, $R^2$ is methyl.

In another embodiment, $R^2$ is benzyl.

In another embodiment, aryl is phenyl, optionally substituted with 1 or 2 substituents selected from the group consisting of methyl, methoxy, fluoro, and trifluoromethyl.

In another embodiment, aryl is phenyl, optionally substituted with 1 or 2 fluoro substituents.

All possible combinations of the above-indicated interesting embodiments are considered to be embraced within the scope of this invention.

Particular compounds may be selected from the group of
5,6-dihydro-2-(phenylethynyl)-7(4H)-benzothiazolone;
2-[(5-fluoro-3-pyridinyl)ethynyl]-5,6-dihydro-7(4H)-benzothiazolone;
6,7-dihydro-2-(phenylethynyl)-thiazolo[5,4-c]pyridin-4 (5H)-one;
6,7-dihydro-5-methyl-2-(phenylethynyl)-thiazolo[5,4-c]pyridin-4(5H)-one;
5,6-dihydro-2-[(E)-2-phenylethenyl]-7(4H)-benzothiazolone;
5,6-dihydro-2-(2-phenylethyl)-7(4H)-benzothiazolone;
2-(4-methyl-3,4-dihydro-2H-1,4-benzoxazin-7-yl)-5,6-dihydro-1,3-benzothiazol-7(4H)-one;
5,6-dihydro-2-(3-pyridinylethynyl)-7(4H)-benzothiazolone;
6,7-dihydro-5-(2-methoxyethyl)-2-(phenylethynyl)-thiazolo[5,4-c]pyridin-4 (5H)-one; and
6,7-dihydro-2-(phenylethynyl)-5-(phenylmethyl)-thiazolo[5,4-c]pyridin-4(5H)-one;

and the pharmaceutically acceptable salts and the solvates thereof.

For therapeutic use, salts of the compounds of Formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable salts are defined to comprise the therapeutically active non-toxic acid addition salt forms that the compounds according to Formula (I) are able to form. Said salts can be obtained by treating the base form of the compounds according to Formula (I) with appropriate acids, for example inorganic acids, for example hydrohalic acid, in particular hydrochloric acid, hydrobromic acid, sulphuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicylic acid, p-aminosalicylic acid and pamoic acid. Conversely said salt forms can be converted into the free base form by treatment with an appropriate base.

The compounds according to Formula (I) containing acidic protons may also be converted into their therapeutically active non-toxic base salt forms by treatment with appropriate organic and inorganic bases. Appropriate base salt forms comprise, for example, the ammonium salts, the alkaline and earth alkaline metal salts, in particular lithium, sodium, potassium, magnesium and calcium salts, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids, for example arginine and lysine.

Conversely, said salt forms can be converted into the free acid forms by treatment with an appropriate acid.

The term solvate comprises the solvent addition forms as well as the salts thereof, which the compounds of Formula (I) are able to form. Examples of such solvent addition forms are e.g. hydrates, alcoholates and the like.

The term "stereochemically isomeric forms" or "stereoisomeric forms" as used hereinbefore or hereinafter, defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. The invention also embraces each of the individual isomeric forms of the compounds of Formula (I) and their salts and solvates, substantially free, i.e. associated with less than 50%, preferably less than 20%, more preferably less than 10%, preferably less than 5%, in particular less than 2% and most preferably less than 1% of the other isomers. Thus, when a compound of Formula (I) is for instance specified as (R), this means that the compound is substantially free of the (S) isomer. Stereogenic centers may have the R- or S-configuration; substituents on bivalent cyclic (partially) saturated radicals may have either the cis- or trans-configuration. Compounds encompassing double bonds can have an E- or Z-stereochemistry at said double bond. Stereisomeric forms of the compounds of Formula (I) are embraced within the scope of this invention.

Following CAS nomenclature conventions, when two stereogenic centers of known absolute configuration are present in a compound, an R or S descriptor is assigned (based on Cahn-Ingold-Prelog sequence rule) to the lowest-numbered chiral center, the reference center. The configuration of the second stereogenic center is indicated using relative descriptors [R*,R*] or [R*,S*], where R* is always specified as the reference center and [R*,R*] indicates centers with the same chirality and [R*,S*] indicates centers of unlike chirality. For example, if the lowest-numbered chiral center in the compound has an S configuration and the second center is R, the stereo descriptor would be specified as S—[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system (hydrogen atom in compounds according to Formula (I)) relative to the position of the highest priority substituent on the reference atom is denominated "α", if it is on the same side of the mean plane determined by the ring system, or "β", if it is on the other side of the mean plane determined by the ring system.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3$H, $^{11}$C, $^{18}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Preparation

The compounds according to the invention can generally be prepared by a succession of steps, each of which is known to the skilled person. In particular, the compounds can be prepared according to the following synthesis methods.

The compounds of Formula (I) may be synthesized in the form of racemic mixtures of enantiomers which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

A. Preparation of the Final Compounds

Experimental Procedure 1

The compounds according to Formula (I-a), wherein A is —C≡C—, can be prepared by a Sonogashira coupling between an intermediate of Formula (II) and an intermediate of Formula (III) according to Reaction Scheme (1a). The reaction is performed in a suitable reaction-inert solvent, such as, for example, DMF, in the presence of a suitable base, such as, for example, triethylamine, a Pd-complex catalyst such as, for example, PdCl$_2$(PPh$_3$)$_2$, under thermal conditions such as, for example, heating the reaction mixture for example at 80° C.-120° C. Alternative Sonogashira reaction conditions can be selected by the person skilled in the art from reaction procedures described in the literature. In Reaction Scheme (1a), all variables are as defined in Formula (I), Z is hydrogen or trimethylsilyl and T is a group suitable for Pd-mediated coupling reactions, such as, for example, halo.

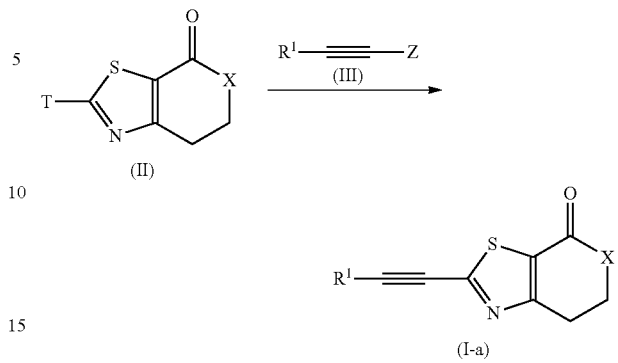

Alternatively, final compounds according to Formula (I-a), wherein A is —C≡C—, can be prepared by a Sonogashira coupling between an intermediate of Formula (IV) and an intermediate of Formula (V) according to Reaction Scheme (1b). The reaction is performed in a suitable reaction solvent, such as, for example, DMF, in the presence of a suitable base, such as, for example, triethylamine, a Pd-complex catalyst such as, for example, PdCl$_2$(PPh$_3$)$_2$, at a moderately high temperature such as for example 60° C.-150° C. Alternative Sonogashira reaction conditions can be selected by the person skilled in the art from reaction procedures described in the literature. In Reaction Scheme (1b), all variables are defined as in Formula (I) and T' is a group suitable for Pd-mediated coupling reactions, such as, for example, halo.

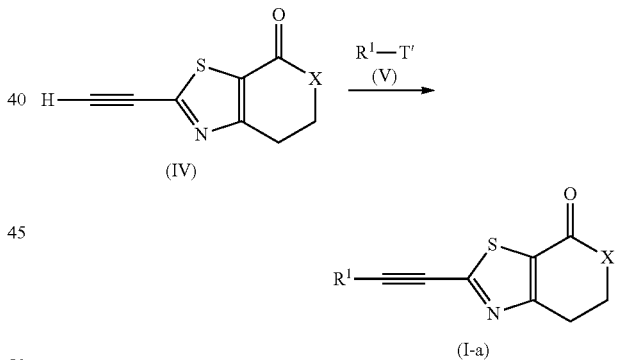

Experimental Procedure 2

The compounds according to Formula (I-b), wherein A is —CH═CH—, can be prepared by reacting an intermediate of Formula (II) with an intermediate of Formula (VI) according to Reaction Scheme (2a). The reaction is performed in a suitable reaction-inert solvent, such as, for example, acetonitrile, in the presence of a suitable base, such as, for example, triethylamine, a Pd-complex catalyst such as, for example, PdCl$_2$(PPh$_3$)$_2$, under thermal conditions such as, for example, heating the reaction mixture for example at 60° C.-120° C. In Reaction Scheme (2a), all variables are as defined in Formula (I) and T is a group suitable for Pd-mediated coupling reactions, such as, for example, halo.

Reaction Scheme 2a

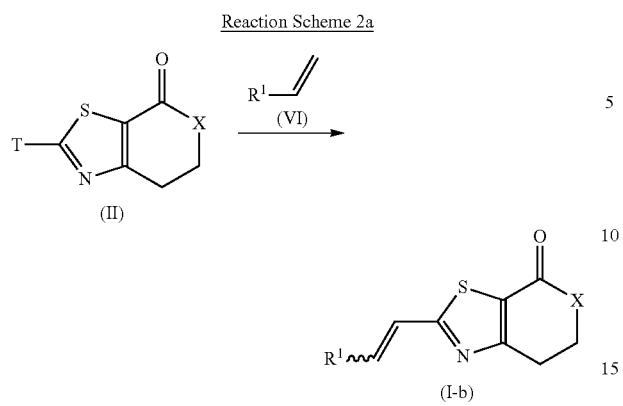

Alternatively, final compounds according to Formula (I-b), wherein A is —CH=CH—, can be prepared by reacting an intermediate of Formula (II) with an intermediate of Formula (VII) according to Reaction Scheme (2b). The reaction is performed in a suitable reaction-inert solvent, such as, for example, 1,4-dioxane or mixtures of inert solvents such as, for example, 1,4-dioxane/DMF, in the presence of a suitable base, such as, for example, aqueous $NaHCO_3$ or $Na_2CO_3$, a Pd-complex catalyst such as, for example, $Pd(PPh_3)_4$ under thermal conditions such as, for example, heating the reaction mixture at 150° C. using microwave irradiation, for example for 10 minutes. In Reaction Scheme (2b), all variables are as defined in Formula (I), and T is a group suitable for Pd mediated coupling reactions, such as, for example, halo. $R^3$ and $R^{3'}$ may be hydrogen or alkyl, or may be taken together to form for example a bivalent radical of formula —$CH_2CH_2$—, —$CH_2CH_2CH_2$—, or —$C(CH_3)_2C(CH_3)_2$—.

Reaction Scheme 2b

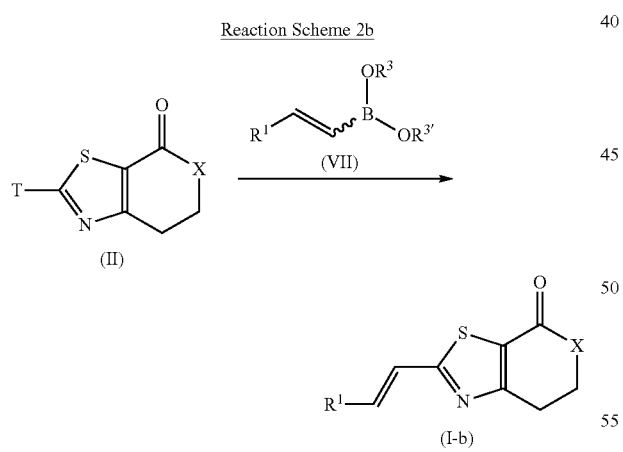

Compounds according to Formula (I-b), wherein A is —CH=CH—, can also be prepared by partial hydrogenation of the triple bond present in the final compounds of Formula (I-a) according to Reaction Scheme (2c). The reaction is performed in a suitable reaction-inert solvent, in the presence of hydrogen and a hydrogenation catalyst, applying reaction conditions that are known by the person skilled in the art. In Reaction Scheme (2c), all variables are as defined in Formula (I).

Reaction Scheme 2c

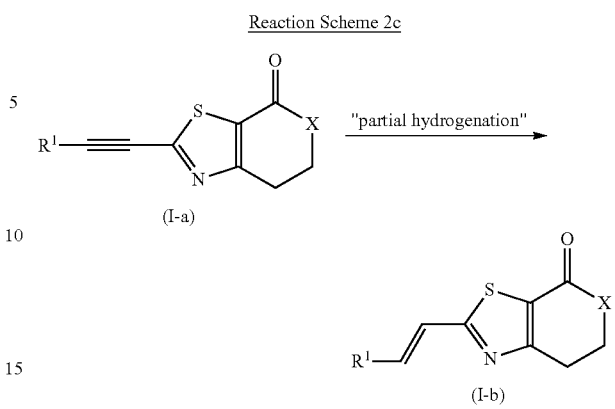

Experimental Procedure 3

Compounds according to Formula (I-c), wherein A is —$CH_2CH_2$—, can be prepared by hydrogenation of the double bond present in the final compounds of Formula (I-b) according to Reaction Scheme (3). The reaction is performed in a suitable reaction-inert solvent, in the presence of hydrogen and a hydrogenation catalyst, applying reaction conditions that are known to the person skilled in the art. In Reaction Scheme (3), all variables are as defined in Formula (I).

Reaction Scheme 3

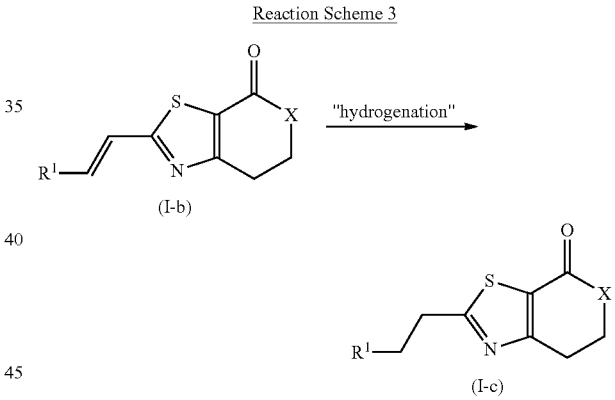

Experimental Procedure 4

Compounds according to Formula (I-d), wherein $R^1$-A together is 3,4-dihydro-2H-1,4-benzoxazin-7-yl optionally substituted with methyl; hereby represented as Z, can be prepared by a Suzuki coupling between an intermediate of Formula (II) with an intermediate of Formula (VIII) according to Reaction Scheme (4). The reaction is performed in a suitable reaction-inert solvent, such as, for example, 1,4-dioxane or mixtures of inert solvents such as, for example, 1,4-dioxane/DMF, in the presence of a suitable base, such as, for example, aqueous $NaHCO_3$ or $Na_2CO_3$, a Pd-complex catalyst such as, for example, $Pd(PPh_3)_4$ under thermal conditions such as, for example, heating the reaction mixture at 150° C. using microwave irradiation, for example for 10 minutes. Alternative Suzuki coupling reaction conditions can be selected by the person skilled in the art from reaction procedures well described in the literature. In Reaction Scheme (4), all variables are as defined in Formula (I), Z is as previously defined, and T is a group suitable for Pd-mediated coupling reactions, such as, for example, halo. $R^3$ and $R^{3'}$ may be hydrogen or alkyl, or may be taken together to form for example the bivalent radical of Formula —$CH_2CH_2$—, —$CH_2CH_2CH_2$—, or —$C(CH_3)_2C(CH_3)_2$—.

Reaction Scheme 4

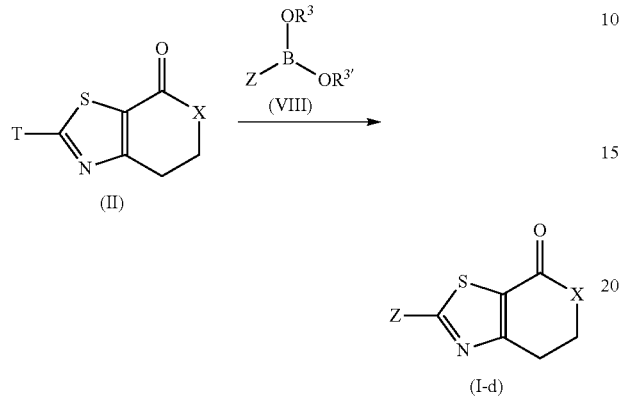

Experimental Procedure 5

Compounds according to Formula (I), wherein A is —O—$C_{1-3}$alkanediyl-, hereby named (I-e) or compounds according to Formula (I) wherein A is —($NR^4$)—$C_{1-3}$alkanediyl-, hereby named (I-f), can be prepared by reacting an intermediate of Formula (II) wherein T is bromo hereby named (II-a) with an alcohol or an amine of Formula (IXa) or (IXb), respectively, according to Reaction Schemes (5a) and (5b). The reaction is performed in a suitable reaction-inert solvent, such as, for example, acetonitrile, in the presence of a suitable base, such as, for example, $Cs_2CO_3$, under thermal conditions such as, for example, heating the reaction mixture at 80° C. for a period of time to allow completion of the reaction, for example overnight. Alternative reaction conditions can be selected by the person skilled in the art from reaction procedures well described in the literature. In Reaction Schemes (5a) and (5b), all variables are as defined in Formula (I) and $R^4$ is hydrogen and m is an integer ranging from 1 to 3.

Reaction Scheme 5a

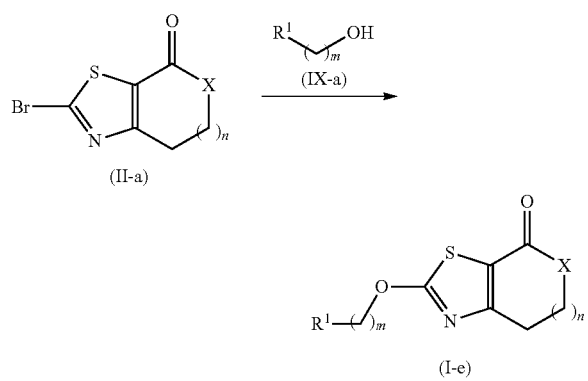

Reaction Scheme 5b

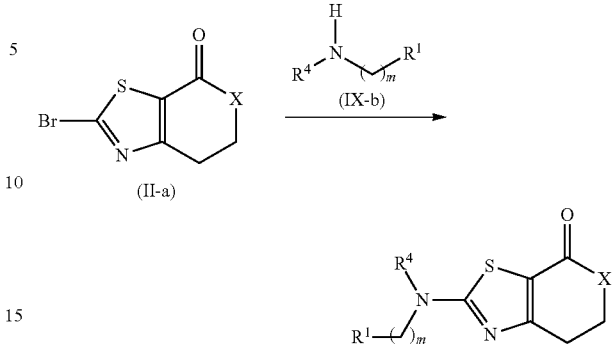

Experimental Procedure 6

Compounds according to Formula (I), wherein A is —O—, hereby named (I-g), can be prepared by reacting an intermediate of Formula (II-a) with an alcohol of Formula (X), respectively according to Reaction Scheme (6). The reaction is performed in a suitable reaction-inert solvent, such as, for example, acetonitrile, in the presence of a suitable base, such as, for example, $Cs_2CO_3$, under thermal conditions such as, for example, heating the reaction mixture at 80° C. for a period of time to allow completion of the reaction, for example overnight. Alternative reaction conditions can be selected by the person skilled in the art from reaction procedures well described in the literature. In Reaction Scheme (6), all variables are as defined in Formula (I).

Reaction Scheme 6

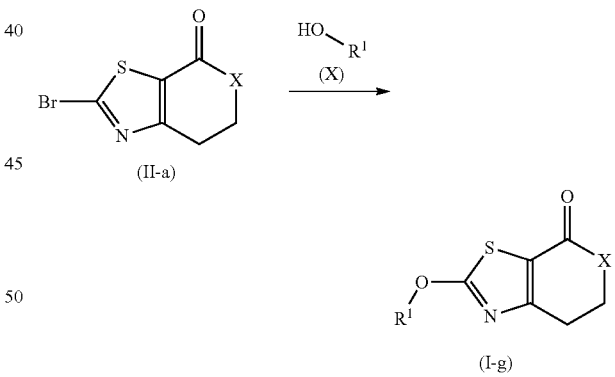

Experimental Procedure 7

Compounds according to Formula (I) wherein X is $NR^2$, hereby named (I-h) can be prepared by a coupling reaction between an intermediate of Formula (I) wherein X is NH, hereby named (I-i) with an intermediate of Formula (XI) according to Reaction Scheme (7). The reaction is performed in a suitable reaction-inert solvent, such as, for example, toluene, in the presence of a suitable base, such as, for example, $Na_2CO_3$, in the presence of a ligand such as for example N,N'-dimethylethylenediamine, in the presence of a copper salt such as, for example, CuI under thermal conditions such as, for example, heating the reaction mixture at 120° C. for a period of time to allow completion of the reaction, for example overnight. The reaction could also be performed in a suitable reaction-inert solvent, such as, for example, acetonitrile or DMF, in the presence of a suitable base, such as, for example, $Cs_2CO_3$ or sodium hydride, under thermal conditions such as, for example, heating the reaction mixture at 80° C. or at low temperature such as 0° C., for a period of time to allow completion of the reaction, for example overnight. Alternatively, reaction conditions can be selected by the person skilled in the art from reaction procedures well described in the literature. In Reaction Scheme (7), all variables are as defined in Formula (I) and Q is a group such as halo.

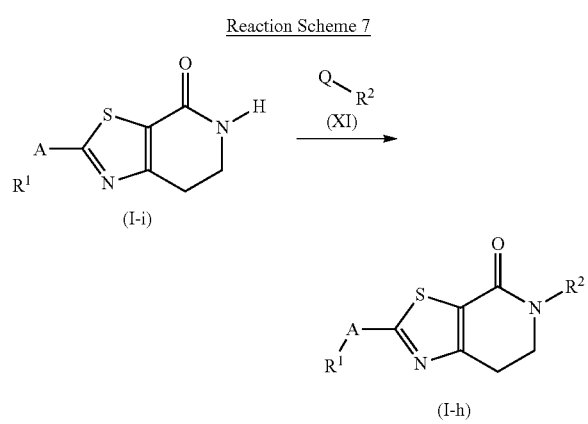

Reaction Scheme 7

B. Preparation of the Intermediate Compounds

Experimental Procedure 8

The intermediates according to Formula (II-a), wherein T is bromo, can be prepared by reaction of an intermediate of Formula (XII) according to Reaction Scheme (8). The reaction is performed with a reagent or mixture of reagents suitable for the transformation of an $NH_2$ group into a halogen atom, such as for example a mixture of copper(II) bromide and 3-methyl-1-nitrosooxy-butane, applying reaction conditions that are known to a person skilled in the art. In reaction scheme (8), all variables are as defined in Formula (I).

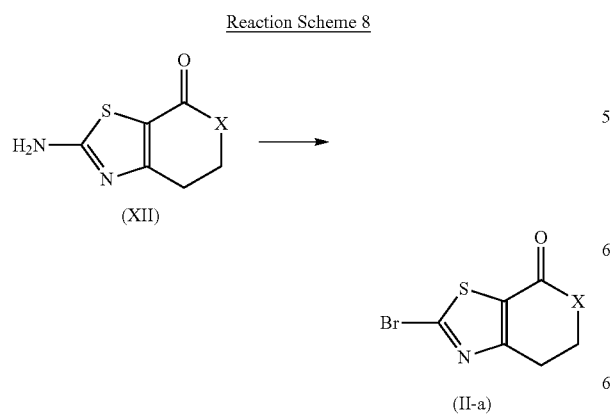

Reaction Scheme 8

Experimental Procedure 9

The intermediates according to Formula (IV) can be prepared by reaction of an intermediate of Formula (XIII) according to reaction scheme (9). The reaction is performed with a reagent suitable for proto-desilylation, such as for example tetrabutylammonium fluoride, applying reaction conditions that are known to a person skilled in the art. In Reaction Scheme (9), all variables are as defined in Formula (I).

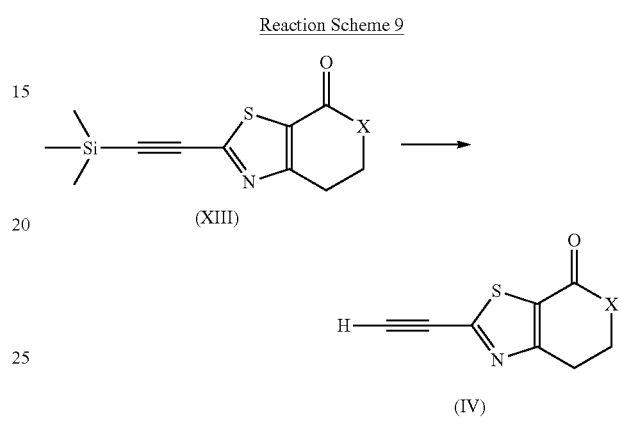

Reaction Scheme 9

Experimental Procedure 10

The intermediates according to Formula (XIII) can be prepared by reacting an intermediate of Formula (II) with trimethylsilylacetylene according to Reaction Scheme (10). The reaction is performed in a suitable reaction-inert solvent, such as, for example, DMF, in the presence of a suitable base, such as, for example, N,N-diisopropylethylamine, a Pd-complex catalyst such as, for example, $Pd(PPh_3)_4$, a phosphine such as, for example, $PPh_3$, a copper salt such as, for example, CuI and under thermal conditions such as, for example, heating the reaction mixture for example at 80° C.-120° C. In Reaction Scheme (10), all variables are as defined in Formula (I) and T is a group suitable for Pd mediated coupling reactions, such as, for example, halo.

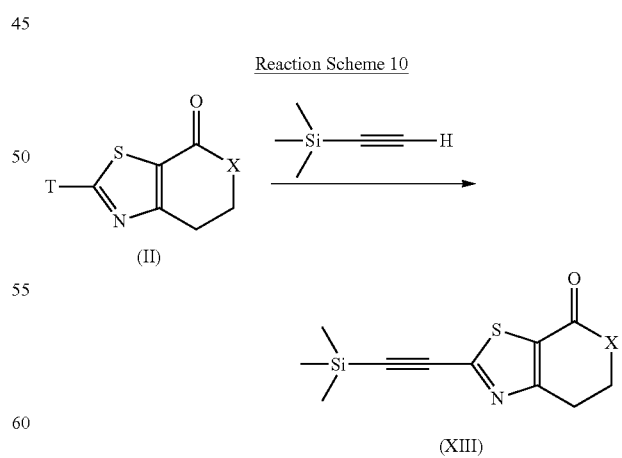

Reaction Scheme 10

Experimental Procedure 11

The intermediates according to Formula (XII), wherein X is $NR^2$, hereby named (XII-a) can be prepared by reaction of an intermediate of Formula (XIV) wherein X is NR², hereby named (XIV-a) with thiourea according to Reaction Scheme (11). The reaction is performed in a reaction-inert solvent, such as for example ethanol, at a moderately high temperature, such as for example 80° C. for a period of time that allows completion of the reaction. In Reaction Scheme (11), all variables are as defined in Formula (I).

Reaction Scheme 11

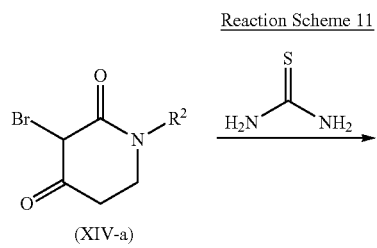

Experimental Procedure 12

The intermediates according to Formula (XIV-a) can be prepared by bromination of an intermediate of Formula (XV) according to Reaction Scheme (12). The reaction is performed in a reaction-inert solvent, such as for example carbon tetrachloride, with a suitable brominating agent, such as for example N-bromosuccinimide, at a moderately low temperature, such as for example 10° C.-15° C. for a period of time that allows completion of the reaction. In Reaction Scheme (12), all variables are as defined in Formula (I).

Reaction Scheme 12

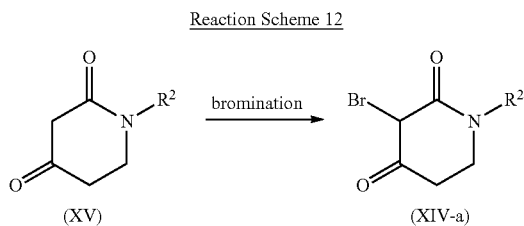

Experimental Procedure 13

The intermediates according to Formula (XV) can be prepared by decarboxylation of an intermediate of Formula (XVI) according to Reaction Scheme (13). The reaction is performed in a reaction-inert solvent, such as for example water, with a suitable acidic agent, such as for example acetic acid, at a moderately high temperature such as 100° C., for a period of time that allows completion of the reaction. In Reaction Scheme (13), all variables are as defined in Formula (I).

Reaction Scheme 13

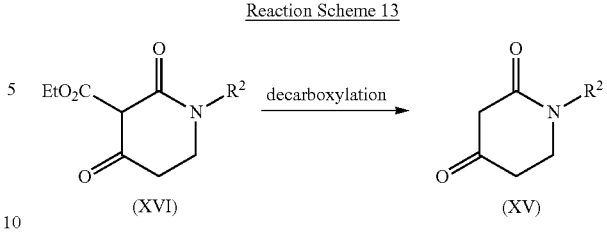

Experimental Procedure 14

The intermediates according to Formula (XVI) can be prepared by reaction of an intermediate of Formula (XVII) according to Reaction Scheme (14). The reaction is performed in a reaction-inert solvent, such as for example ethanol, with a suitable base, such as for example sodium ethoxide, at a moderately high temperature such as 85° C., for a period of time that allows completion of the reaction. In Reaction Scheme (14), all variables are as defined in Formula (I).

Reaction Scheme 14

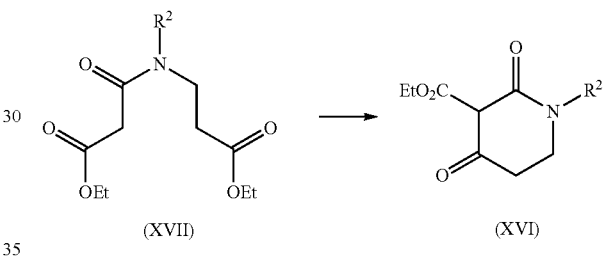

Experimental Procedure 15

The intermediates according to Formula (XVII) can be prepared by reaction of an intermediate of Formula (XVIII) with ethyl malonyl chloride according to Reaction Scheme (15). The reaction is performed in a reaction-inert solvent, such as for example dichloromethane, with a suitable base, such as for example triethylamine, at a low temperature such as 0° C., for a period of time that allows completion of the reaction. In Reaction Scheme (15), all variables are as defined in Formula (I).

Reaction Scheme 15

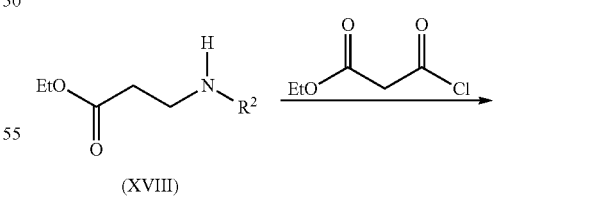

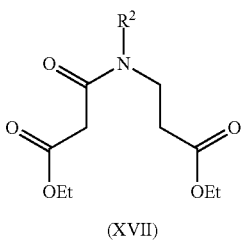

Experimental Procedure 16

The intermediates according to Formula (XVIII) can be prepared by reaction of the appropriate amine of Formula (XIX) with ethyl acrylate according to Reaction Scheme (16). The reaction is performed in a reaction-inert solvent, such as for example ethanol, with a suitable acid, such as for example hydrochloric acid, at a high temperature such as 90° C., for a period of time that allows completion of the reaction. In Reaction Scheme (16), all variables are as defined in Formula (I).

Reaction Scheme 16

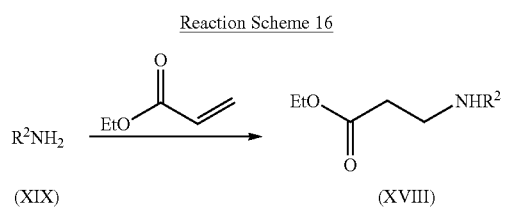

Experimental Procedure 17

The intermediates according to Formula (XII), wherein X is N—H hereby named (XII-b), can be prepared from an intermediate of Formula (XX) according to reaction scheme (17). The reaction is performed with a suitable reagent for the cleavage of the tert-butoxycarbonyl group such as for example hydrochloric acid, applying reaction conditions that are known to a person skilled in the art. In reaction scheme (17), all variables are as defined in Formula (I).

Reaction Scheme 17

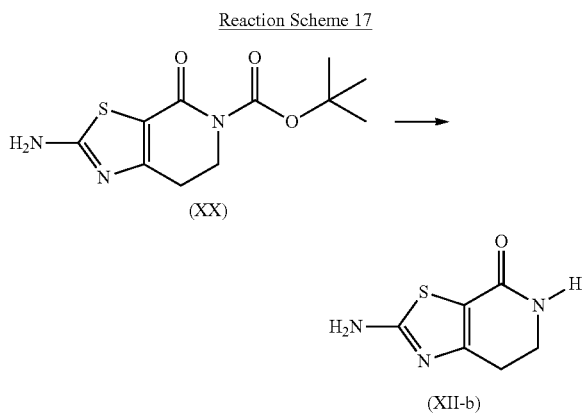

Experimental Procedure 18

The intermediates according to Formula (XX) can be prepared by reaction of an intermediate of Formula (XXI) with thiourea according to reaction scheme (18). The reaction is performed in a reaction-inert solvent, such as for example ethanol, at a moderately high temperature, such as for example 80° C. for a period of time that allows completion of the reaction. In reaction scheme (18), all variables are as defined in Formula (I).

Reaction Scheme 18

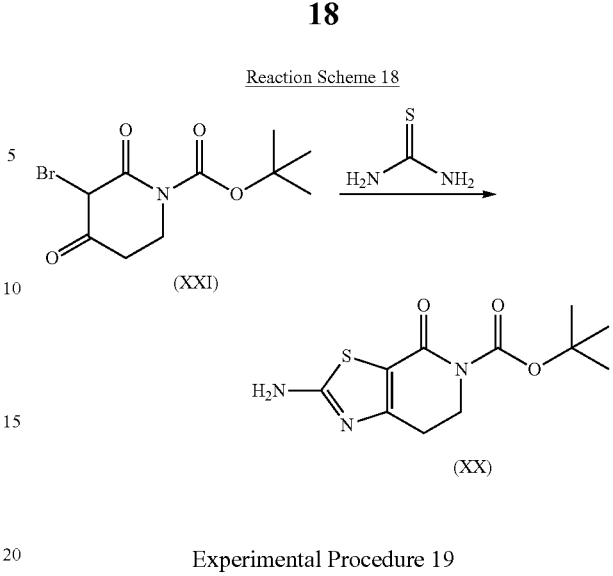

Experimental Procedure 19

The intermediates according to Formula (XXI) can be prepared by bromination of an intermediate of Formula (XXII) according to reaction scheme (19). The reaction is performed in a reaction-inert solvent, such as for example carbon tetrachloride, with a suitable bromination agent, such as for example N-bromosuccinimide, at a moderately low temperature, such as for example 10° C.-15° C. for a period of time that allows completion of the reaction. In reaction scheme (19), all variables are as defined in Formula (I).

Reaction Scheme 19

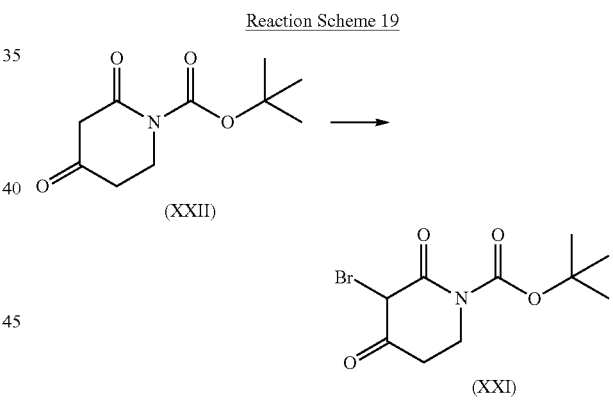

The starting materials according to Formulae (III), (V), (VI), (VII), (VIII) and (XXII) are compounds that are either commercially available or may be prepared according to conventional reaction procedures well known to anyone skilled in the art.

Thus, intermediates of Formula (III) can be prepared as for example as it is described in *Chem. Rev.* 2007, 107(3), 874-922; *Chem. Rev.* 2006, 106(12), 5387-5412 and references cited therein or are commercially available.

Thus, intermediates of Formula (VII) can be prepared as for example as it is described in *J. Am. Chem. Soc.* 2002, 124(27), 8001-8006; *J. Org. Chem.* 2008, 73(14), 5589-5591; *Org. Leu.* 2008, 10(5), 811-814 and references cited therein or are commercially available.

Thus intermediates of Formula (VIII) can be prepared, for example, as it is described in *J. Org. Chem.* 2008, 73(14), 5589-5591; and references cited therein or are commercially available.

Thus intermediates of Formula (XI) and Formula (XIX) can be obtained commercially.

Thus intermediates of Formula (XII-a) can be obtained commercially.

Pharmacology

The compounds provided in this invention are positive allosteric modulators of metabotropic glutamate receptors, in particular they are positive allosteric modulators of mGluR5. The compounds of the present invention do not appear to bind to the glutamate recognition site, the orthosteric ligand site, but instead to an allosteric site. In the presence of glutamate or an agonist of mGluR5, the compounds of this invention increase the mGluR5 response. The compounds provided in this invention are expected to have their effect at mGluR5 by virtue of their ability to increase the response of such receptors to glutamate or mGluR5 agonists, enhancing the response of the receptor.

As used herein, the term "treatment" is intended to refer to all processes, wherein there may be a slowing, interrupting, arresting or stopping of the progression of a disease, but does not necessarily indicate a total elimination of all symptoms.

Hence, the present invention relates to a compound according to the present invention the stereoisomeric forms thereof and the pharmaceutically acceptable acid or base addition salts and the solvates thereof, for use as a medicine or for use as a medicament.

The invention also relates to the use of a compound according to the general Formula (I), the stereoisomeric forms thereof and the pharmaceutically acceptable acid or base addition salts and the solvates thereof, or a pharmaceutical composition according to the invention for the manufacture of a medicament, as well as to the use of a compound according to the invention or a pharmaceutical composition according to the invention for the manufacture of a medicament for treating or preventing, in particular treating, a condition in a mammal, including a human, the treatment or prevention of which is affected or facilitated by the neuromodulatory effect of allosteric modulators of mGluR5, in particular positive allosteric modulators thereof.

The invention also relates to a compound according to the general Formula (I), the stereoisomeric forms thereof and the pharmaceutically acceptable acid or base addition salts and the solvates thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR5, in particular positive allosteric modulators thereof.

The present invention also relates to a compound according to the general Formula (I), the stereoisomeric forms thereof and the pharmaceutically acceptable acid or base addition salts and the solvates thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is affected or facilitated by the neuromodulatory effect of positive allosteric modulators of mGluR5.

Also, the present invention relates to the use of a compound according to the general Formula (I), the stereoisomeric forms thereof and the pharmaceutically acceptable acid or base addition salts and the solvates thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR5.

The present invention also relates to a compound according to the present invention or a pharmaceutical composition according to the invention for use in the manufacture of a medicament for treating or preventing, in particular treating, a condition in a mammal, including a human, the treatment or prevention of which is affected or facilitated by the neuromodulatory effect of allosteric modulators of mGluR5, in particular positive allosteric modulators thereof. The present invention also relates to a compound according to the present invention or a pharmaceutical composition according to the invention for treating or preventing, in particular treating, a condition in a mammal, including a human, the treatment or prevention of which is affected or facilitated by the neuromodulatory effect of allosteric modulators of mGluR5, in particular positive allosteric modulators thereof.

Also, the present invention relates to the use of a compound according to the invention or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR5.

Where the invention is said to relate to the use of a compound or composition according to the invention for the manufacture of a medicament for e.g. the treatment of a mammal, it is understood that such use is to be interpreted in certain jurisdictions as a method of e.g. treatment of a mammal, comprising administering to a mammal in need of such e.g. treatment, an effective amount of a compound or composition according to the invention.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance tolerance, substance withdrawal (including substances such as, for example, opiates, nicotine, tobacco products, alcohol, benzodiazepines, cocaine, sedatives, hypnotics, etc.), psychosis, schizophrenia (including positive, negative and cognitive symptoms thereof), anxiety (including generalized anxiety disorder, panic disorder, and obsessive compulsive disorder), mood disorders (including depression, mania, bipolar disorders), trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder Preferably, the central nervous system disorder is a personality disorder selected from the group of obsessive-compulsive personality disorder and schizoid, schizotypal disorder.

Preferably, the central nervous system disorder is a substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, substance-induced persisting dementia and mild cognitive impairment.

Of the disorders mentioned above, the treatment of schizophrenia and dementia are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a compound according to the general Formula (I), the stereoisomeric forms thereof and the pharmaceutically acceptable acid or base addition salts and the solvates thereof, for use in the treatment of any one of the diseases mentioned hereinbefore.

The invention also relates to a compound according to the general Formula (I), the stereoisomeric forms thereof and the pharmaceutically acceptable acid or base addition salts and the solvates thereof, for use in treating any one of the diseases mentioned hereinbefore.

The invention also relates to a compound according to the general Formula (I), the stereoisomeric forms thereof and the pharmaceutically acceptable acid or base addition salts and the solvates thereof, for the treatment or prevention, in particular treatment, of any one of the diseases mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

The compounds of the present invention can be administered to mammals, preferably humans, for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore, and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form thereof and a pharmaceutically acceptable addition salt or solvate thereof, to warm-blooded animals, including humans.

Therefore, the invention also relates to a method for the prevention and/or treatment of any one of the diseases mentioned hereinbefore comprising administering a therapeutically effective amount of a compound according to the invention to a patient in need thereof.

One skilled in the art will recognize that a therapeutically effective amount of the PAMs of the present invention is the amount sufficient to modulate the activity of the mGluR5 and that this amount varies inter alia, depending on the type of disease, the concentration of the compound in the therapeutic formulation, and the condition of the patient. Generally, an amount of PAM to be administered as a therapeutic agent for treating diseases in which modulation of the mGluR5 is beneficial, such as the disorders described herein, will be determined on a case by case by an attending physician.

Generally, a suitable dose is one that results in a concentration of the PAM at the treatment site in the range of 0.5 nM to 200 µM, and more usually 5 nM to 50 µM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Because such positive allosteric modulators of mGluR5, including compounds of Formula (I), enhance the response of mGluR5 to glutamate, it is an advantage that the present methods utilize endogenous glutamate.

Because positive allosteric modulators of mGluR5, including compounds of Formula (I), enhance the response of mGluR5 to agonists, it is understood that the present invention extends to the treatment of neurological and psychiatric disorders associated with glutamate dysfunction, such as for example those mentioned hereinbefore, by administering an effective amount of a positive allosteric modulator of mGluR5, including compounds of Formula (I), in combination with an mGluR5 agonist.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

Pharmaceutical Compositions

The present invention also provides compositions for preventing or treating diseases in which modulation of the mGluR5 receptor is beneficial, such as the disorders described herein. While it is possible for the active ingredient to be administered alone, it is preferable to present it as a pharmaceutical composition. Accordingly, the invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, an effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for administration orally, rectally, percutaneously, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example surfactants, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

The amount of a compound of Formula (I) that can be combined with a carrier material to produce a single dosage form will vary depending upon the disease treated, the mammalian species, and the particular mode of administration. However, as a general guide, suitable unit doses for the compounds of the present invention can, for example, preferably contain between 0.1 mg to about 1000 mg of the active compound. A preferred unit dose is between 1 mg to about 500 mg. A more preferred unit dose is between 1 mg to about 300 mg. Even more preferred unit dose is between 1 mg to about 100 mg. Such unit doses can be administered more than once a day, for example, 2, 3, 4, 5 or 6 times a day, but preferably 1 or 2 times per day, so that the total dosage for a 70 kg adult is in the range of 0.001 to about 15 mg per kg weight of subject per administration. A preferred dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

As already mentioned, the invention also relates to a pharmaceutical composition comprising the compounds according to the invention and one or more other drugs in the treatment, prevention, control, amelioration, or reduction of risk of diseases or conditions for which compounds of Formula (I) or the other drugs may have utility as well as to the use of such a composition for the manufacture of a medicament. The use of such a composition for the manufacture of a medicament in the treatment, prevention, control, amelioration or reduction of risk of diseases or conditions for which compounds of Formula (I) or the other drugs may have utility is also contemplated. The present invention also relates to a combination of a compound according to the present invention and a mGluR5 orthosteric agonist. The present invention also relates to such a combination for use as a medicine. The present invention also relates to a product comprising (a) a compound according to the present invention, a pharmaceutically acceptable salt thereof or a solvate thereof, and (b) a mGluR5 orthosteric agonist, as a combined preparation for simultaneous, separate or sequential use in the treatment or prevention of a condition in a mammal, including a human, such as for example a condition mentioned hereinbefore, the treatment or prevention of which is affected or facilitated by the neuromodulatory effect of mGluR5 allosteric modulators, in particular positive mGluR5 allosteric modulators. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Experimental Part

Several methods for preparing the compounds of this invention are illustrated in the following Examples. Unless otherwise noted, all starting materials were obtained from commercial suppliers and used without further purification.

Hereinafter, the term 'm.p.' means melting point, 'THF' means tetrahydrofuran, 'DMF' means dimethylformamide, 'DCM' means dichloromethane, 'ACN' means acetonitrile, 'AcOEt' means ethylacetate, 'AcOH' means acetic acid, 'EtOH' means ethanol, 'MeOH' means methanol.

Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Open column chromatography was performed on silica gel, particle size 60 Å, mesh=230-400 (Merck) using standard techniques. Automated flash column chromatography was performed using ready-to-connect cartridges from Merck, on irregular silica gel, particle size 15-40 µm (normal phase disposable flash columns) on a SPOT or LAFLASH system from Armen Instrument.

A. Preparation of the Intermediates

Example A1

Preparation of Intermediate 1

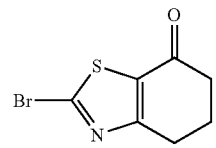 [SMILES: O=C1CCCc2nc(Br)sc21]

A mixture of 2-amino-5,6-dihydro-4H-benzothiazol-7-one (19 g, 112 mmol), copper (II) bromide (27 g, 120 mmol) and 3-methyl-1-nitrosooxy-butane (18 g, 153 mmol) in ACN (250 mL) was heated at 80° C. for 1 hour. The reaction mixture was then cooled to room temperature and poured into a 10% solution of HCl. The mixture was extracted with DCM and the organic layer was separated, dried (Na$_2$SO$_4$), filtered and the solvent evaporated in vacuo to yield 19.6 g (75%) of intermediate 1 that was used in the next step without further purification.

Example A2

Preparation of Intermediate 2

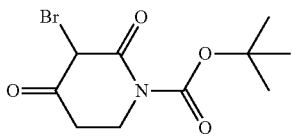 [SMILES: CC(C)(C)OC(=O)N1CCC(=O)C(Br)C1=O]

To a mixture of 2,4-dioxo-piperidine-1-carboxylic acid tert-butyl ester (40 g, 187.58 mmol) in carbon tetrachloride (500 mL) was added N-bromosuccinimide (33.38 g, 187.58 mmol) portionwise keeping the reaction temperature in the range of 10° C.-15° C. The mixture was further stirred at 10° C.-15° C. for 2 hours. The reaction mixture was allowed to warm to room temperature and the solvents evaporated in vacuo. The residue thus obtained was dissolved in AcOEt and washed with $H_2O$. The organic layer was separated, dried ($Na_2SO_4$), filtered and the solvent evaporated in vacuo to yield 30 g (55%) of racemic intermediate 2 that was used in the next step without further purification.

Example A3

Preparation of Intermediate 3

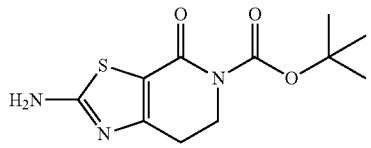 [SMILES: CC(C)(C)OC(=O)N1CCc2nc(N)sc2C1=O]

A mixture of intermediate 2 (25 g, 85.6 mmol), thiourea (6.5 g, 85.6 mmol) and $NaHCO_3$ (7.2 g, 85.6 mmol) in EtOH (400 mL) was heated at 80° C. for 2.5 hours. The reaction mixture was then cooled to room temperature and the solids were filtered off. The filtrate was evaporated in vacuo to give a residue that was crystallized in EtOH. The yellow crystals thus obtained were filtered off and dried to yield 15 g (66%) of intermediate 3.

Example A4

Preparation of Intermediate 4

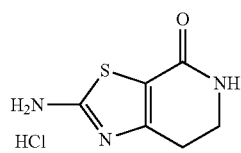 [SMILES: Cl ; Nc1nc2c(s1)C(=O)NCC2]

A solution of intermediate 3 (15 g, 55.6 mmol) in a 4M solution of HCl in 1,4-dioxane (100 mL) was stirred at room temperature for 30 minutes. The solvent was evaporated in vacuo to yield 10 g (95%) of intermediate 4 as a yellow powder which was used in the next step without further purification.

Example A5

Preparation of Intermediate 5

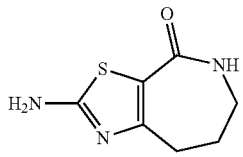 [SMILES: Nc1nc2c(s1)C(=O)NCCC2]

To a stirred solution of 2-amino-5,6-dihydro-4H-benzothiazol-7-one (10 g, 59 mmol) in chloroform (250 mL) was added concentrated $H_2SO_4$ at room temperature. Sodium azide (7.6 g, 117 mmol) was then carefully added to the mixture over two hours (vigorous gas evolution). The reaction mixture was further stirred at room temperature for 48 hours. The mixture was poured into crushed ice and a saturated solution of $NaHCO_3$ was added until the pH of the solution was about 9. The formed precipitate was filtered off and washed with $H_2O$ and AcOEt. The solid was dried in the oven (T=50° C.) to yield 9 g (83%) of intermediate 5 that was used in the next step without further purification.

Example A6

Preparation of Intermediate 6

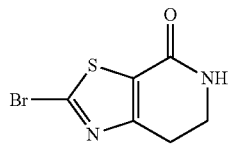 [SMILES: O=C1NCCc2nc(Br)sc21]

A mixture of intermediate 4 (8 g, 39.8 mmol), copper (II) bromide (10.43 g, 46.68 mmol) and 3-methyl-1-nitrosooxy-butane (6.8 g, 58.35 mmol) in ACN (100 mL) was stirred at room temperature for 1.5 hours. The solvent was evaporated in vacuo. The residue thus obtained was dissolved in AcOEt and washed with $H_2O$. The organic layer was separated, dried ($Na_2SO_4$), filtered and the solvent evaporated in vacuo to yield 5 g (55%) of intermediate 6 that was used in the next step without further purification.

Example A7

Preparation of Intermediate 7

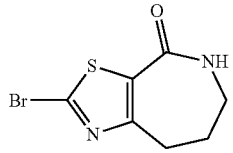 [SMILES: O=C1NCCCc2nc(Br)sc21]

A mixture of intermediate 5 (20 g, 109 mmol), copper (II) bromide (24 g, 107 mmol) and 3-methyl-1-nitrosooxy-butane (33.5 g, 286 mmol) in ACN (250 mL) was heated at 80° C. for 1 hour. The reaction mixture was then cooled to room temperature and poured into a 10% solution of HCl. The mixture was extracted with DCM and the organic layer was separated, dried (Na$_2$SO$_4$), filtered and the solvent evaporated in vacuo to yield 23 g (87%) of intermediate 7 that was used in the next step without further purification.

Example A8

Preparation of Intermediate 8

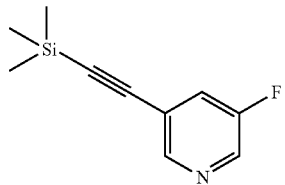

To a solution of 3-bromo-5-fluoropyridine (5 g, 28.4 mmol), trimethylsilylacetylene (3.35 g, 34 mmol) and copper (I) iodide (0.13 g, 0.68 mmol) in a mixture of THF (45 mL) and triethylamine (22.5 mL) at room temperature was added PdCl$_2$(PPh$_3$)$_2$ (0.48 g, 0.68 mmol). The reaction mixture was stirred at room temperature for 14 hours under a nitrogen atmosphere, then concentrated in vacuo. The residue thus obtained was purified by flash column chromatography (silica; petroleum ether/AcOEt 10:1). The desired fractions were collected and the solvent was evaporated in vacuo to yield 0.9 g (16%) of intermediate 8 as a brown oil.

Example A9

Preparation of Intermediate 9

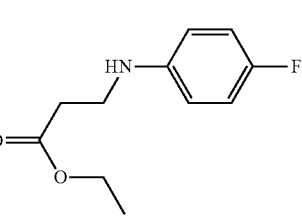

To a solution of 4-fluoroaniline (11.5 ml, 121.4 mmol) in AcOH (7 mL) was added ethyl acrylate (15.85 mL, 145.68 mmol). The mixture was stirred at 90° C. for 18 hours in a sealed tube. The reaction mixture was allowed to warm to room temperature and then was poured onto cooled water, basified by a 10% solution of Na$_2$CO$_3$ addition and extracted with DCM. The organic layer was separated, dried (Na$_2$SO$_4$), filtered and the solvent evaporated in vacuo. The residue was purified by flash column chromatography (silica; AcOEt in Heptane 0/100 to 10/90). The desired fractions were collected and evaporated in vacuo to yield 24.6 g (66%) of intermediate 9.

Example A10

Preparation of Intermediate 10

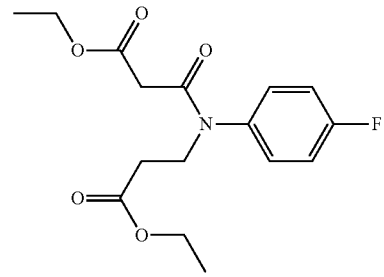 [SMILES: CCOC(=O)CCN(C(=O)CC(=O)OCC)c1ccc(F)cc1]

To a solution of intermediate 9 (10 g, 47.34 mmol) in DCM (10 mL), ethyl malonyl chloride (7.88 mL, 61.54 mmol) and N,N-diisopropylethylamine (16.49 mL, 94.68 mmol) were added. The mixture was stirred at room temperature for 1 hour and then diluted with further DCM and washed with a saturated solution of NH$_4$Cl. The organic layer was separated, dried (Na$_2$SO$_4$), filtered and the solvent evaporated in vacuo. The crude product was purified by flash column chromatography (silica; AcOEt in Heptane 0/100 to 20/80). The desired fractions were collected and the solvents evaporated in vacuo to yield 11 g (71%) of intermediate 11 as an orange oil.

Example A11

Preparation of Intermediate 11

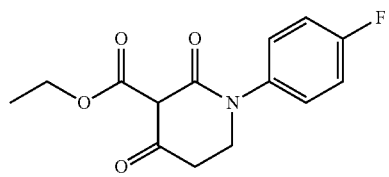 [SMILES: CCOC(=O)C1C(=O)CCN(c2ccc(F)cc2)C1=O]

A mixture of intermediate 10 (6.27 g, 19.27 mmol) in a 21% solution of sodium ethoxide in EtOH (14.39 mL, 38.55 mmol) was stirred at 85° C. for 16 hours. The solvent was evaporated in vacuo and the residue was partitioned between AcOEt and H$_2$O. The aqueous layer was separated, acidified by 1 N HCl solution addition and extracted with DCM. The organic layer was separated, dried (Na$_2$SO$_4$), filtered and the solvent evaporated in vacuo to yield 5 g (93%) of intermediate 11 used in next step without any further purification.

Example A12

Preparation of Intermediate 12

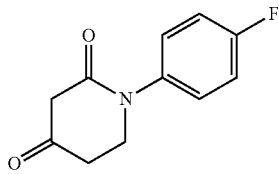 [SMILES: O=C1CCN(c2ccc(F)cc2)C(=O)C1]

A solution of intermediate 11 (7.5 g, 26.86 mmol) in a mixture of AcOH (0.6 mL) and H$_2$O (59.4 mL) was stirred at 90° C. for 16 hours. The reaction mixture was dried (MgSO$_4$), filtered and the solvent evaporated in vacuo to yield 5.5 g (99%) of intermediate 12 used in next step without any further purification.

Example A13

Preparation of Intermediate 13

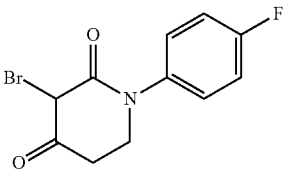 [SMILES: O=C1CCN(c2ccc(F)cc2)C(=O)C1Br]

To a solution of intermediate 12 (5.5 g, 26.54 mmol) in DCM (60 mL) at 0° C., N-bromosuccinimide (5.2 g, 29.2 mmol) was added. The mixture was stirred at 0° C. for 30 minutes and the solvent evaporated in vacuo to yield 7.7 g (>100%) of intermediate 13 used in next step without any further purification.

Example A14

Preparation of Intermediate 14

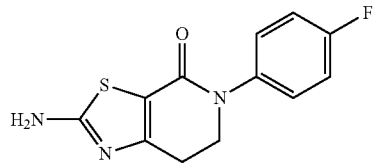 [SMILES: Nc1nc2c(s1)C(=O)N(c1ccc(F)cc1)CC2]

A mixture of intermediate 13 (4.14 g, 14.48 mmol), thiourea (1.1 g, 14.48 mmol) and NaHCO$_3$ (1.22 g, 14.48 mmol) in ethanol (60 mL) was heated at 80° C. for 1 hour. The reaction mixture was then cooled to room temperature and the solids were filtered off. The filtrate was concentrated under vacuum to yield 3.1 g (81%) of intermediate 14 used in next step without any further purification.

Example A15

Preparation of Intermediate 15

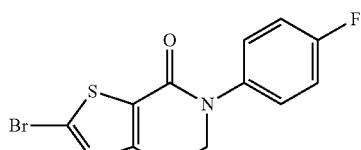

A mixture of intermediate 14 (3 g, 11.39 mmol), copper (II) bromide (3.05 g, 13.67 mmol) and 3-methyl-1-nitrosooxy-butane (2.3 mL, 17.09 mmol) in ACN (80 mL) was stirred at room temperature for 45 minutes. The reaction mixture was then concentrated in vacuo. The residue thus obtained was partitioned between AcOEt and H$_2$O. The organic layer was separated, dried (Na$_2$SO$_4$), filtered and the solvent evaporated in vacuo. The residue was purified by flash column chromatography (silica; AcOEt in Heptane 0/100 to 30/70). The desired fractions were collected and the solvents evaporated in vacuo to yield 1.2 g (32%) of intermediate 15 as a white solid.

B. Preparation of the Final Compounds

Example B1

Preparation of Compound 1

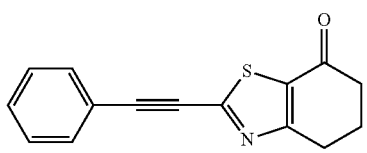 [SMILES: O=C1CCCc2nc(C#Cc3ccccc3)sc21]

To a solution of intermediate 1 (2.3 g, 9.86 mmol), phenylacetylene (2.01 g, 19.7 mmol), copper (I) iodide (0.2 g, 1.05 mmol) and triethylamine (2.98 g, 29.58 mmol) in 1,4-dioxane (50 mL) at room temperature was added [1,1'-bis(diphenylphosphino)ferrocene]dichloro-palladium(II) (0.2 g, 0.245 mmol). The reaction mixture was stirred at reflux for 2 hours under a nitrogen atmosphere. The reaction mixture was then cooled to room temperature and the volatiles were evaporated in vacuo. The crude product was purified by flash column chromatography (silica; petroleum ether/AcOEt 1:2). The desired fractions were collected and the solvent was evaporated in vacuo to yield 1.2 g (52%) of compound 1 as a solid. $^1$H NMR (400 MHz, CDCl$_3$) δ ppm 2.28 (quin, J=6.4 Hz, 2H), 2.70 (t, J=6.3 Hz, 2H), 3.13 (t, J=6.1 Hz, 2H), 7.39-7.53 (m, 3H), 7.60-7.70 (m, 2H).

Example B2

Preparation of Compound 2

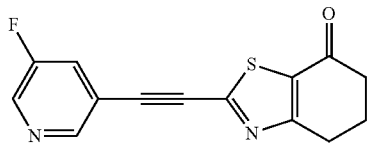

To a solution of intermediate 1 (0.2 g, 0.86 mmol), intermediate 8 (0.25 g, 1.29 mmol), copper (I) iodide (0.006 g, 0.034 mmol) and $PdCl_2(PPh_3)_2$ (0.012 g, 0.017 mmol) in THF (8 mL) at room temperature was added tetrabutylammonium fluoride (2.58 mL, 2.58 mmol; 1M solution in THF) under a nitrogen atmosphere. The reaction mixture was stirred at room temperature for 14 hours then concentrated in vacuo. The crude product was purified by flash column chromatography (silica; petroleum ether/AcOEt 5:1). The desired fractions were collected and the solvent was evaporated in vacuo to yield compound 2 (101.5 mg, 43% yield) as a yellow solid. $^1$H NMR (300 MHz, $CDCl_3$) δ ppm 2.19 (quin, J=6.4 Hz, 2H), 2.50-2.72 (m, 2H), 3.04 (t, J=6.2 Hz, 2H), 7.55 (dd, J=8.3, 1.3 Hz, 1H), 8.50 (br. s., 1H), 8.63 (br. s., 1H).

Example B3

Preparation of Compound 3

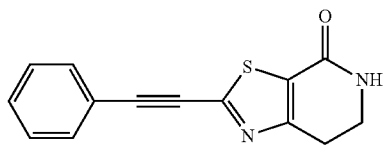

To a solution of intermediate 6 (2.33 g, 10 mmol), phenylacetylene (2.0 g, 20 mmol) and triethylamine (4.5 g, 45 mmol) in 1,4-dioxane (50 mL) at room temperature were added [1,1'-bis(diphenylphosphino)ferrocene]dichloro-palladium(II) (0.73 g, 1 mmol) and copper (I) iodide (0.75 g, 4 mmol) under a nitrogen atmosphere. The reaction mixture was stirred at 80° C. for 2 hours under a nitrogen atmosphere, then cooled to room temperature and concentrated in vacuo. The resulting residue was dissolved in AcOEt and washed with $H_2O$. The organic layer was separated, dried ($Na_2SO_4$), filtered and the solvent evaporated in vacuo. The crude product was purified by flash column chromatography (silica; petroleum ether/AcOEt 10:1 to 1:1). The desired fractions were collected and the solvent was evaporated in vacuo to yield compound 3 (0.7 g, 30% yield) as a brown solid. $^1$H NMR (400 MHz, DMSO-$d_6$) δ ppm 3.00 (t, J=7.0 Hz, 2H), 3.50 (td, J=7.0, 2.5 Hz, 2H), 7.44-7.57 (m, 3H), 7.63-7.72 (m, 2H), 8.07 (br. s., 1H).

Example B4

Preparation of Compound 4

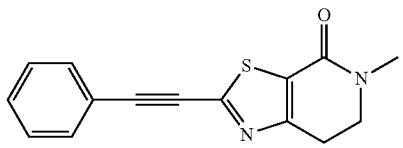

A mixture of compound 3 (0.25 g, 0.98 mmol), methyl iodide (0.84 g, 5.9 mmol) and cesium carbonate (1.9 g, 5.9 mmol) in ACN (50 mL) was stirred at 80° C. overnight. The reaction mixture was then cooled to room temperature and concentrated in vacuo. The crude product was purified by reverse phase HPLC (gradient elution:0.1% TFA in ACN/0.1% TFA in $H_2O$). The desired fractions were collected, washed with $NaHCO_3$ (aqueous saturated solution) and extracted with AcOEt. The combined organic extracts were dried ($Na_2SO_4$), filtered and the solvent evaporated in vacuo to yield compound 4 (50.3 mg, 19% yield). $^1$H NMR (400 MHz, DMSO-$d_6$) δ ppm 2.97 (s, 3H), 3.09 (t, J=7.2 Hz, 2H), 3.67 (t, J=7.2 Hz, 2H), 7.43-7.58 (m, 3H), 7.67 (d, J=6.8 Hz, 2H).

Example B5

Preparation of Compound 5

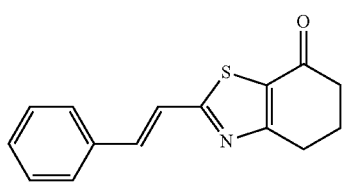 [SMILES: O=C1CCCc2nc(/C=C/c3ccccc3)sc21]

To a solution of intermediate 1 (0.6 g, 2.6 mmol), trans-2-phenylboronic acid (0.38 g, 2.6 mmol) and $Na_2CO_3$ (0.54 g, 5.2 mmol) in 1,2-dimethoxyethane (9 mL) and $H_2O$ (3 mL), at room temperature, was added $Pd(PPh_3)_4$ (0.09 g, 0.06 mmol). The reaction mixture was stirred at 80° C. overnight under a nitrogen atmosphere. The reaction mixture was then cooled to room temperature, diluted with $H_2O$ (15 mL) and extracted with AcOEt (15 mL). The organic layer was separated, dried ($Na_2SO_4$), filtered and the solvent evaporated in vacuo. The crude product was purified by column chromatography (silica; petroleum ether/AcOEt 5:1). The desired fractions were collected and the solvent was evaporated in vacuo to yield compound 5 (350 mg, 52% yield).

Example B6

Preparation of Compound 6

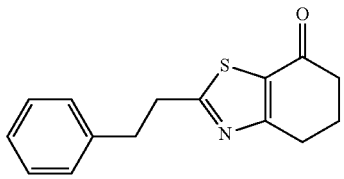

10% Palladium on charcoal (0.035 g) was added to a solution of compound 5 (0.35 g, 1.37 mmol) in THF (10 mL). The mixture was hydrogenated at room temperature overnight. The catalyst was filtered off and the filtrate was evaporated in vacuo. The crude product was purified by reverse phase HPLC (gradient elution: 0.1% TFA in ACN/0.1% TFA in $H_2O$). The desired fractions were collected, washed with $NaHCO_3$ (aqueous saturated solution) and extracted with AcOEt. The organic layer was separated, dried ($Na_2SO_4$), filtered and the solvent evaporated in vacuo affording compound 6 (120 mg, 34% yield) as an oil. $^1$H NMR (300 MHz, METHANOL-$d_4$) δ ppm 2.20 (quin, J=6.3 Hz, 2H), 2.61 (t, J=6.6 Hz, 2H), 3.02 (t, J=6.1 Hz, 2H), 3.12 (t, J=7.3 Hz, 2H), 3.33-3.41 (m, 2H), 7.15-7.34 (m, 5H).

Example B7

Comparative Example

Preparation of Compound 7 (Comparative Example)

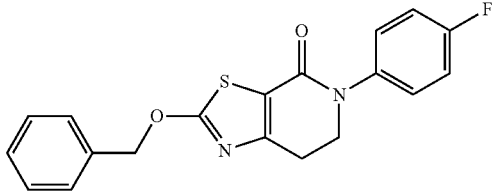 [SMILES: O=C1c2sc(OCc3ccccc3)nc2CCN1c1ccc(F)cc1]

Benzyl alcohol (0.38 mL, 3.67 mmol) was added dropwise to a suspension of 60% sodium hydride in mineral oils (0.183 g, 4.58 mmol) in THF (12 mL), under a nitrogen atmosphere. The mixture was stirred at room temperature for 15 minutes and then intermediate 15 (1 g, 3.06 mmol) was added. The mixture was stirred at 120° C. for 25 minutes in a sealed tube under microwave irradiation. The mixture was partitioned between DCM and $H_2O$. The organic layer was separated, dried ($MgSO_4$), filtered and the solvent evaporated in vacuo. The residue was purified by flash column chromatography (silica; AcOEt in DCM in Heptane 0/0/100 to 10/10/80), the desired fractions were collected and evaporated in vacuo to yield 0.68 g (63%) of compound 7 as a white solid. $C_{19}H_{15}FN_2O_2S$ $^1$H NMR (400 MHz, $CDCl_3$) δ ppm 3.08 (t, J=6.9 Hz, 2 H), 4.01 (t, J=6.9 Hz, 2H), 5.49 (s, 2H), 7.08 (t, J=8.7 Hz, 2H), 7.29 (dd, J=9.0, 4.9 Hz, 2H), 7.34-7.54 (m, 5H).

Example B8

Preparation of Compound 8

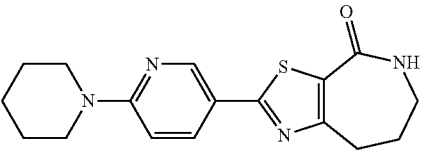 [SMILES: O=C1NCCCc2nc(-c3ccc(N4CCCCC4)nc3)sc21]

$Pd(PPh_3)_4$ (0.02 g, 0.013 mmol) was added to a solution of intermediate 7 (0.2 g, 0.809 mmol), 5'-(4,4,5,5-tetramethyl-[1,3,2]dioxaborolan-2-yl)-3,4,5,6-tetrahydro-2H-[1,2']bipyridinyl (0.23 g, 0.809 mmol) and $Na_2CO_3$ (1 mL, 2M solution in $H_2O$) in a mixture of 1,2-dimethoxyethane (3 mL) and EtOH (1 mL) at room temperature. The reaction mixture was stirred at reflux for 12 hours under a nitrogen atmosphere. The reaction mixture was then cooled to room temperature and AcOEt and $H_2O$ were added. The organic layer was separated, washed successively with water and brine, dried ($Na_2SO_4$) and the solvent evaporated in vacuo. The residue thus obtained was treated with MeOH (30 mL). The yellow precipitate thus formed was filtered off and dried in vacuo affording compound 8 (165 mg, 97% yield). $^1$H NMR (300 MHz, METHANOL-$d_4$) δ ppm 1.60-1.80 (m, 6H), 2.10-2.20 (m, 2H), 3.22 (t, J=6.4 Hz, 2 H), 3.37 (d, J=1.5 Hz, 1H), 3.40-3.48 (m, 2H), 3.65-3.75 (m, 4H), 6.87 (d, J=9.2 Hz, 1H), 8.00 (dd, J=9.0, 2.6 Hz, 1H), 8.67 (d, J=2.3 Hz, 1H).

Example B9

Preparation of Compound 9

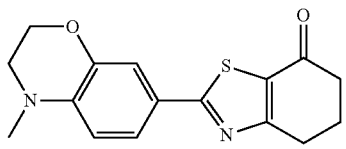 [SMILES: CN1CCOc2cc(-c3nc4c(s3)C(=O)CCC4)ccc21]

$Pd(PPh_3)_4$ (0.03 g, 0.02 mmol) was added to a solution of intermediate 1 (0.2 g, 0.865 mmol), 4-methyl-7-(4,4,5,5-tetramethyl-[1,3,2]dioxaborolan-2-yl)-3,4-dihydro-2H-benzo[1,4]oxazine (0.23 g, 0.865 mmol) and $Na_2CO_3$ (0.23 g, 0.865 mmol) in a mixture of 1,2-dimethoxyethane (3 mL) and $H_2O$ (1 mL) at room temperature. The reaction mixture was stirred at 80° C. overnight under a nitrogen atmosphere, then cooled to room temperature and AcOEt (5 mL) added. The organic layer was separated, washed with $H_2O$, dried ($Na_2SO_4$) and the solvent evaporated in vacuo. The residue thus obtained was purified by reverse phase HPLC (gradient elution: 0.1% TFA in ACN/0.1% TFA in $H_2O$). The desired fractions were collected, washed with $NaHCO_3$ (aqueous saturated solution) and extracted with AcOEt (2×100 mL). The combined organic extracts were dried ($Na_2SO_4$) and evaporated in vacuo affording compound 9 (28 mg, 11% yield). $^1$H NMR (300 MHz, $CDCl_3$) δ ppm 2.09-2.22 (m, 2H), 2.51-2.59 (m, 2 H), 2.92 (s, 3H), 3.00 (t, J=6.1 Hz, 2H), 3.30-3.36 (m, 2H), 4.20-4.25 (m, 2H), 6.58 (d, J=8.3 Hz, 1H), 7.34 (d, J=2.3 Hz, 1H), 7.47-7.54 (m, 1H).

Table 1 and Table 2 list the compounds that were prepared according to the above Examples.

TABLE 1

Structure: 2-(R¹-A-)-6,7-dihydrobenzo[d]thiazol-4(5H)-one scaffold with R¹—A substituent at position 2

| Co. No. | Ex. No. | ----A—R¹ |
|---|---|---|
| 1 | B1 | phenylethynyl (phenyl-C≡C-) |
| 2 | B2 | (5-fluoropyridin-3-yl)ethynyl |
| 5 | B5 | (E)-styryl (phenyl-CH=CH-) |
| 6 | B6 | 2-phenylethyl (phenyl-CH₂-CH₂-) |
| 9 | B9 | 4-methyl-3,4-dihydro-2H-benzo[b][1,4]oxazin-7-yl |
| 10 | B1 | pyridin-3-ylethynyl |

TABLE 2

Structure: 2-(R¹-A-)-5-R²-5,6-dihydrothiazolo[5,4-c]pyridin-4(7H)-one scaffold

| Co. No. | Ex. No. | n | ----A—R¹ | ----R² |
|---|---|---|---|---|
| 3 | B3 | 1 | phenylethynyl | ----H |
| 4 | B4 | 1 | phenylethynyl | ----CH₃ |
| 11 | B4 | 1 | phenylethynyl | -CH₂CH₂-O-CH₃ |
| 12 | B4 | 1 | phenylethynyl | benzyl (-CH₂-C₆H₅) |

TABLE 1a

Additional compounds that can also be prepared according to the examples.

| Co. No. | Ex. No. | n | ----A—R¹ | R² | Salt data |
|---|---|---|---|---|---|
| Comparative example 7 | B7 | 1 | benzyloxy (PhCH₂-O-) | 4-fluorophenyl | |
| 8 | B8 | 2 | 6-(piperidin-1-yl)pyridin-3-yl | ----H | |

TABLE 1a-continued

Additional compounds that can also be prepared according to the examples.

[Structure: thiazole fused with a ring containing N-R², C=O, with A-R¹ substituent and (CH₂)ₙ]

| Co. No. | Ex. No. | n | ----A—R¹ | R² | Salt data |
|---|---|---|---|---|---|
| 13 | B7 | 1 | 2-fluorophenoxy | ----H | Trifluoroacetate |
| 14 | B7 | 1 | 3-(trifluoromethoxy)phenoxy | ----H | Trifluoroacetate |
| 15 | B7 | 1 | 3-fluorophenoxy | ----H | Trifluoroacetate |
| 16 | B7 | 1 | 3-chlorophenoxy | ----H | Trifluoroacetate |
| 17 | B7 | 1 | 3-methoxyphenoxy | ----H | Trifluoroacetate |
| 18 | B7 | 1 | 4-cyanophenoxy | ----H | Trifluoroacetate |
| 19 | B7 | 1 | 3-cyanophenoxy | ----H | Trifluoroacetate |
| 20 | B7 | 1 | 5-(3-fluorophenyl)-1,2,4-oxadiazol-3-yl | ----CH₃ | |
| 21 | B7 | 1 | (pyridin-4-yl)methoxy | 4-fluorophenyl | |
| 22 | B7 | 1 | benzylamino | 4-fluorophenyl | |
| 23 | B7 | 1 | (pyridin-3-yl)methoxy | 2,4-difluorophenyl | |

TABLE 1a-continued

Additional compounds that can also be prepared according to the examples.

| Co. No. | Ex. No. | n | ----A—R¹ | R² | Salt data |
|---|---|---|---|---|---|
| 24 | B7 | 1 | (pyridin-2-yl)methoxy- | 2,4-difluorophenyl | |

C. Analytical Part

LCMS

For (LC)MS-characterization of the compounds of the present invention, the following methods were used.

General Procedure 1

The HPLC measurement was performed using an Agilent 1100 module comprising a pump, a diode-array detector (DAD) (wavelength used 220 nm), and a column as specified in the respective methods below. Column flow was split to an Agilent MSD Series G1946C and G1956A. MS detector was configured with API-ES (atmospheric pressure electrospray ionization). Mass spectra were acquired in only positive ionization mode or in positive/negative modes by scanning from 100 to 1000 umas. The capillary needle voltage was 2500 V for positive ionization mode and 3000 V for negative ionization mode. Fragmentation voltage was 50 V. Drying gas temperature was maintained at 350° C. at a flow of 10 L/min.

Method A

In addition to general procedure 1: Reversed phase HPLC was carried out on a YMC-Pack ODS-AQ, 50×2.0 mm 5 μm column with a flow rate of 0.8 mL/min. A gradient with two mobile phases (A: water with 0.1% TFA; B: ACN with 0.05% TFA) was used in a total 7.5 minutes run. Typical injection volumes of 2 μL were used. Oven temperature was 50° C.

Method B

In addition to general procedure 1: Reversed phase HPLC was carried out on an Ultimate XB-C18, 50×2.1 mm 5 μm column with a flow rate of 0.8 mL/min. A gradient with two mobile phases (A: 10 mmol/L $NH_4HCO_3$; B: ACN) was used in a total 7.5 minutes run. Typical injection volumes of 2 μL were used. Oven temperature was 50° C.

General Procedure 2

The HPLC (Ultra Performance Liquid Chromatography) measurement was performed using an Acquity HPLC (Waters) system comprising a sampler organizer, a binary pump with degasser, a four column's oven, a diode-array detector (DAD) and a column as specified in the respective methods below. Column flow was used without split to the MS detector. The MS detector was configured with an ESCI dual ionization source (electrospray combined with atmospheric pressure chemical ionization). Nitrogen was used as the nebulizer gas. Low-resolution mass spectra (single quadrupole, SQD detector) were acquired in positive/negative ionization modes by scanning from 100 to 1000 in 0.1 seconds using an inter-channel delay of 0.08 seconds. The capillary needle voltage was 3 kV. The cone voltage was 25V for positive ionization mode and 30V for negative ionization mode. The source temperature was maintained at 140° C.

Method C

In addition to the general procedure 2: Reversed phase HPLC was carried out on a BEH-C18 column (1.7 μm, 2.1× 50 mm) from Waters, with a flow rate of 1.0 mL/min, at 50° C. without split to the MS detector. A gradient with two mobile phases (A: 0.5 g/L ammonium acetate solution+5% ACN, B: ACN), were used in a total-5.0 minutes run. Injection volume 0.5 or 2.0 μL.

Method D

Preparative RP-HPLC purification: Purification by RP-HPLC was performed on a custom HP1100 automated purification system with collection triggered by mass detection or using a Gilson Inc. preparative UV-based system using a Phenomenex Luna® C18 column (50×30 mm I.D., 5 μm) with an acetonitrile (unmodified)-water (0.1% TFA) custom gradient.

Reversed phase Agilent LC-MS was performed using a J-Sphere80-C18, 3.0×50 mm, 4.1 min gradient, 5% $CH_3CN$/$H_2O$ (with 0.05% TFA in both mobile phases) to 100% $CH_3CN$.

General Procedure 3

The HPLC measurement was performed using a Shimadzu LCMS 2010 module comprising a pump, a diode-array detector (DAD), a column heater and a column as specified in the respective methods below. Flow from the column was split to the MS detector that was configured with API-ES (atmospheric pressure electrospray ionization).

Method E

In addition to general procedure 3: Reversed phase UHPLC was carried out on a Phenomenex synergi, 30×2.0 mm 2.5 μm column with a flow rate of 0.9 mL/min. A gradient with two mobile phases (A: water with 0.1% TFA; B: ACN with 0.05% TFA) was used to run a gradient condition from 90% A and 10% B to 20% A and 80% B in 0.9, then to 0% A and 100% B up to 1.5 minutes and equilibrated to initial conditions at 1.55 minutes until 2.0 minutes. Typical injection volumes of 1 μL were used. Oven temperature was 60° C., (MS polarity: positive).

Melting Points

Values are either peak values or melt ranges, and are obtained with experimental uncertainties that are commonly associated with this analytical method.

DSC

For a number of compounds, melting points (m.p.) were determined with a Diamond DSC (PerkinElmer). Melting points were measured with a temperature gradient of 10° C./minute. Maximum temperature was 300° C. (indicated by DSC in Table 3). Values are peak values.

WRS-2A

For a number of compounds, melting points (m.p.) were determined with a WRS-2A melting point apparatus (Shanghai Precision and Scientific Instrument Co. Ltd.). Melting points were measured with a linear heating up rate of 0.2-5.0° C./minute. The reported values are melt ranges. The maximum temperature was 300° C. (indicated by WRS-2A in Table 3).

FP

For a number of compounds, melting points were determined in open capillary tubes either on a Mettler FP62 or on a Mettler FP81HT-FP90 apparatus. Melting points were measured with a temperature gradient of 10° C./minute. Maximum temperature was 300° C. The melting point was read from a digital display.

Nuclear Magnetic Resonance (NMR)

For a number of compounds, $^1$H NMR spectra were recorded either on a Bruker DPX-400 or on a Bruker AV-500 spectrometer with standard pulse sequences, operating at 400 MHz and 500 MHz, respectively. Chemical shifts (δ) are reported in parts per million (ppm) downfield from tetramethylsilane (TMS), which was used as internal standard.

TABLE 3

Analytical data.

| Comp. No. | $R_t$ | $[M + H]^+$ | Method | Melting Point |
|---|---|---|---|---|
| 1 | 5.49 | 254 | A | 117.1° C.-119.9° C. (DSC) |
| 2 | 4.81 | 273 | A | 139.2° C.-141.9° C. (DSC) |
| 3 | 5.0 | 255 | A | 232.1° C.-235.1° C. (DSC) |
| 4 | 5.29 | 269 | A | 146.1° C.-147.2° C. (WRS-2A) |
| 5 | 1.317 | 256 | E | n.d. |
| 6 | 5.26 | 258 | B | n.d. |
| 8 | 3.99 | 329 | A | 260.3° C.-264.0° C. (DSC) |
| 9 | 5.29 | 301 | A | 218.1° C.-220.8° C. (DSC) |
| 10 | 4.56 | 255 | A | 109.5° C.-112.0° C. (DSC) |
| 11 | 6.01 | 313 | A | 144.5° C.-148.2° C. (DSC) |
| 12 | 5.9 | 345 | A | 141.5° C.-152.5° C. (DSC) |

$R_t$ means retention time (in minutes),
$[M + H]^+$ means the protonated mass of the compound, method refers to the method used for (LC)MS,
n.d. means not determined TABLE 3a Analytical data for additional compounds.

| Comp. No. | $R_t$ | $[M + H]^+$ | Method | Melting Point |
|---|---|---|---|---|
| Comparative example 7 | 2.44 | 355 | C | 130° C. |
| 13 | 2.501 | 265 | D | n.d. |
| 14 | 2.957 | 331 | D | n.d. |
| 15 | 2.559 | 265 | D | n.d. |
| 16 | 2.77 | 281 | D | n.d. |
| 17 | 2.521 | 277 | D | n.d. |
| 18 | n.d. | n.d. | n.d. | n.d. |
| 19 | 2.357 | 272 | D | n.d. |
| 20 | 1.88 | 331 | C | n.d. |
| 21 | 4.04 | 356 | A | 169.1-170.9° C.(WRS-2A) |
| 22 | 1.96 | 354 | C | 221.3° C. (FP) |
| 23 | 4.51 | 374 | A | 106.0-110.0° C.(WRS-2A) |
| 24 | 5 | 374 | A | 98.1-100.1° C.(WRS-2A) |

$R_t$ means retention time (in minutes),
$[M + H]^+$ means the protonated mass of the compound, method refers to the method used for (LC)MS,
n.d. means not determined.

D. Pharmacological Examples

The compounds provided in the present invention are positive allosteric modulators of mGluR5. These compounds appear to potentiate glutamate responses by binding to an allosteric site other than the glutamate binding site. The response of mGluR5 to a concentration of glutamate is increased when compounds of Formula (I) are present. Compounds of Formula (I) are expected to have their effect substantially at mGluR5 by virtue of their ability to enhance the function of the receptor. The behaviour of positive allosteric modulators tested at mGluR5 using the intracellular $Ca^{2+}$ mobilization binding assay method described below and which is suitable for the identification of such compounds.

In brief, the human mGluR5 receptor was stably expressed in HEK-293 cells and grown at a density of 40,000 cells/well in PDL-coated 384-well plates. Cells were preloaded with the calcium-sensing dye Fluo-4 AM and various concentrations of test compound were added in the absence of exogenous glutamate to test for direct agonist activity. Shortly (2.5 min) thereafter, an $EC_{20}$ equivalent of glutamate (~0.2 μM) was added. The fluorescence signal was monitored using a Hamamatsu Functional Drug Screening System (FDSS) fluorescence plate reader following the addition of compound alone (direct agonist response) and then the further addition of an $EC_{20}$ of glutamate (positive allosteric modulation response). The $pEC_{50}$ was defined as the negative log of the test compound concentration which produced an increase in the glutamate $EC_{20}$-mediated response that was 50% of maximum. Individual amplitudes were expressed as % effect by multiplying each amplitude by 100 and then dividing the product by the mean of the amplitudes derived from the glutamate $EC_{Max}$-treated wells. $E_{max}$ values reported in this application are defined as the maximum % effect obtained in a concentration-response curve.

TABLE 4

Pharmacological data for compounds according to the invention

| Co. No. | $pEC_{50}$ | $E_{max}$ (%) |
|---|---|---|
| 1 | 7.29 | 100 |
| 2 | 5.37 | 83 |
| 3 | 6.66 | 78 |
| 4 | 7.16 | 79 |
| 6 | 4.73 | 51 |
| 9 | 5.20 | 77 |
| 10 | 5.82 | 92 |
| 11 | 6.56 | 64 |
| 12 | 6.33 | 90 |

The pharmacological data for compound 8 was $pEC_{50}$=5.30, $E_{max}$=11% in the same assay.

A $pEC_{50}$ of <4.52 was estimated for compounds 13-24 in similar in vitro assays.

E. Prophetic Composition Examples

"Active ingredient" as used throughout these examples relates to a final compound of formula (I), the pharmaceutically acceptable salts thereof, the solvates and the stereochemically isomeric forms thereof.

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |

-continued

| | | |
|---|---|---|
| Talcum | 10 | mg |
| Magnesium stearate | 5 | mg |
| Potato starch | ad 200 | mg |

In this Example, active ingredient can be replaced with the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable

A parenteral composition is prepared by stirring 1.5% by weight of active ingredient of the invention in 10% by volume propylene glycol in water.

4. Ointment

| | | |
|---|---|---|
| Active ingredient | 5 to 1000 | mg |
| Stearyl alcohol | 3 | g |
| Lanoline | 5 | g |
| White petroleum | 15 | g |
| Water | ad 100 | g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound of formula (I)

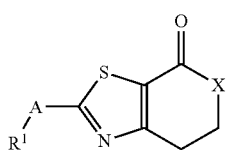

(I)

or a stereoisomeric form thereof,
wherein
X is $NR^2$;
A is selected from the group consisting of 1,2-ethanediyl; 1,2-ethenediyl; and 1,2-ethynediyl;
$R^1$ is selected from the group consisting of phenyl; phenyl substituted with 1 or 2 halo substituents; pyridinyl; and pyridinyl substituted with 1 or two halo substituents;
$R^2$ is selected from the group consisting of hydrogen; methyl; methoxyethyl; aryl; benzyl; and benzyl wherein the phenyl part is substituted with 1 or 2 halo substituents;
  wherein aryl is phenyl, optionally substituted with 1 or 2 substituents selected from the group consisting of methyl, methoxy, cyano, fluoro, chloro, trifluoromethyl and trifluoromethyloxy;
or a pharmaceutically acceptable salt thereof.

2. The compound according to claim 1, wherein
A is selected from the group consisting of 1,2-ethanediyl; 1,2-ethenediyl; and 1,2-ethynediyl;
$R^1$ is selected from the group consisting of phenyl; phenyl substituted with 1 or 2 halo substituents; pyridinyl; and pyridinyl substituted with 1 or two halo substituents;
$R^2$ is selected from the group consisting of hydrogen; methyl; methoxyethyl; benzyl; and benzyl wherein the phenyl part is substituted with 1 or 2 halo substituents;
or a pharmaceutically acceptable salt thereof.

3. The compound according to claim 1, wherein
A is selected from the group consisting of 1,2-ethenediyl; and 1,2-ethynediyl;
$R^1$ is selected from the group consisting of phenyl; phenyl substituted with 1 or 2 halo substituents; pyridinyl; and pyridinyl substituted with 1 or two halo substituents;
$R^2$ is selected from the group consisting of hydrogen; methyl; methoxyethyl; benzyl; and benzyl wherein the phenyl part is substituted with 1 or 2 halo substituents;
or a pharmaceutically acceptable salt thereof.

4. The compound according to claim 1, wherein
A is selected from the group consisting of 1,2-ethenediyl; and 1,2-ethynediyl;
$R^1$ is selected from the group consisting of phenyl; pyridinyl; and pyridinyl substituted with 1 or two fluoro substituents;
$R^2$ is selected from the group consisting of hydrogen; methyl; methoxyethyl; benzyl; and benzyl wherein the phenyl part is substituted with 1 or 2 fluoro substituents;
or a pharmaceutically acceptable salt thereof.

5. The compound according to claim 1, wherein
A is selected from the group consisting of 1,2-ethenediyl; and 1,2-ethynediyl;
$R^1$ is selected from the group consisting of phenyl; pyridinyl; and pyridinyl substituted with 1 or two fluoro substituents;
$R^2$ is selected from the group consisting of hydrogen; methyl; methoxyethyl; and benzyl;
or a pharmaceutically acceptable salt thereof.

6. A compound according to claim 1, selected from the group consisting of
2-[(5-fluoro-3-pyridinyl)ethynyl]-5,6-dihydro-7(4H)-benzothiazolone;
6,7-dihydro-2-(phenylethynyl)-thiazolo[5,4-c]pyridin-4 (5H)-one;
6,7-dihydro-5-methyl-2-(phenylethynyl)-thiazolo[5,4-c] pyridin-4(5H)-one;
6,7-dihydro-5-(2-methoxyethyl)-2-(phenylethynyl)-thiazolo[5,4-c]pyridin-4(5H)-one; and
6,7-dihydro-2-(phenylethynyl)-5-(phenylmethyl)-thiazolo[5,4-c]pyridin-4(5H)-one;
or a pharmaceutically acceptable salt thereof.

7. A pharmaceutical composition comprising a therapeutically effective amount of a compound as defined in claim 1 and a pharmaceutically acceptable carrier.

* * * * *